United States Patent [19]

Janoff et al.

[11] Patent Number: 4,880,635
[45] Date of Patent: Nov. 14, 1989

[54] DEHYDRATED LIPOSOMES

[75] Inventors: Andrew S. Janoff, Yardley, Pa.; Pieter R. Cullis; Marcel B. Bally, both of Vancouver, Canada; Michael W. Fountain, Griggstown; Richard S. Ginsberg, Monroe, both of N.J.; Michael J. Hope; Thomas D. Madden, both of Vancouver, Canada; Hugh P. Schieren, Yardley, Pa.; Regina L. Jablonski, Trenton, N.J.

[73] Assignee: The Liposome Company, Inc., Princeton, N.J.

[21] Appl. No.: 759,419

[22] Filed: Jul. 26, 1985

Related U.S. Application Data

[63] Continuation-in-part of Ser. No. 638,809, Aug. 8, 1984, abandoned, and a continuation-in-part of Ser. No. 749,161, Jun. 26, 1985, abandoned.

[51] Int. Cl.[4] .............................................. A61K 37/22
[52] U.S. Cl. ...................................................... 424/450
[58] Field of Search ......................... 264/4.1, 4.3, 4.6; 428/402.2; 424/417, 450

[56] References Cited

U.S. PATENT DOCUMENTS

| | | | |
|---|---|---|---|
| 3,962,429 | 6/1976 | Furuno et al. | 424/181 |
| 4,053,585 | 10/1977 | Allison et al. | 424/92 |
| 4,193,983 | 3/1980 | Ullman et al. | 424/12 |
| 4,217,344 | 8/1980 | Vanlerberghe et al. | 424/60 |
| 4,229,360 | 10/1980 | Schneider et al. | 260/403 |
| 4,235,871 | 11/1980 | Papahadjopoulos et al. | 424/19 |
| 4,241,046 | 12/1980 | Papahadjopoulos et al. | 424/19 |
| 4,370,349 | 1/1983 | Evans et al. | 424/365 |
| 4,389,330 | 6/1983 | Tice et al. | 427/213.36 |
| 4,411,894 | 10/1983 | Schrank et al. | 424/199 |
| 4,438,052 | 3/1984 | Weder et al. | 264/4.6 |
| 4,460,577 | 7/1984 | Moro et al. | 424/180 |
| 4,485,045 | 11/1984 | Regen | 260/403 |
| 4,485,054 | 11/1984 | Mezei et al. | 264/4.6 |
| 4,515,736 | 5/1985 | Deamer | 264/4.3 |

FOREIGN PATENT DOCUMENTS

| | | |
|---|---|---|
| 3335701 | 4/1984 | Denmark . |
| 0094692 | 11/1983 | European Pat. Off. . |
| 82-82311 | 5/1982 | Japan . |
| 2134869 | 8/1984 | United Kingdom . |

OTHER PUBLICATIONS

Chemical Abstract 103:92759a (Madden et al.).
Chemical Abstract 103:67036e (MacDonald).
Chemical Abstract 102:84326w (Kirby et al.).
Bally et al., 2985, Biochim. Biophys. Acta., 812:66, "Uptake of Safranine and Other Lipophilic Cations into Model Membrane Systems in Response to a Membrane Potential".

(List continued on next page.)

Primary Examiner—Douglas W. Robinson
Assistant Examiner—Richard Kearse
Attorney, Agent, or Firm—Allen Bloom; Catherine L. Kurtz

[57] ABSTRACT

Dehydrated liposomes are prepared by drying liposome preparations under reduced pressure in the presence of one or more protective sugars, e.g., the disaccharides trehalose and sucrose. Preferably, the protective sugars are present at both the inside and outside surfaces of the liposome membranes. Freezing of the liposome preparation prior to dehydration is optional. Alternatively, the protective sugar can be omitted if: (1) the liposomes are of the type which have multiple lipid layers; (2) the dehydration is done without prior freezing; and (3) the dehydration is performed to an end point which results in sufficient water being left in the preparation (e.g., at least 12 moles water/mole lipid) so that the integrity of a substantial portion of the multiple lipid layers is retained upon rehydration. Concentration gradients capable of generating transmembrane potentials can be created across the liposome membranes either before or after dehydration, and the transmembrane potentials resulting from these gradients can be used to load charged materials, e.g., drugs, into the liposomes.

9 Claims, 9 Drawing Sheets

OTHER PUBLICATIONS

Gruner, 1985, Biochemistry, 24;2833, "Novel Multilayered Lipid Vesicles: Comparison of Physical Characteristics of Multilamellar Liposomes and Stable Plurilamellar Vesicles."

Garcia et al., Biochemistry, 1983, 22(10):2524, "Mechanism of Lactose Translocation in Proteoliposomes Reconstituted with Lac Carrier Protein Purified from Eshericia coli. 1. Effect of pH and Imposed Membrane Potential on Efflux, Exchange, and Counterflow."

Shakhov et al., 1984, Biokhimika, 48(8):1347, "Reconstitution of Highly Purified Proton-Translocating Pyrothosphatase."

Kirby et al., 1984, Bio/Technology, 2(11)979, "Dehydration-Rehydration Vesicles: A Simple Method for High Yield Drug Entrapment in Liposomes."

Crommelen et al., 1983, Int. J. Pharm., 16(1):79, "Preparation and Characterization of Doxorubicin-Containing Liposomes: I. Influence of Liposome Charge and pH of Hydration Medium on Loading Capacity and Particle Size."

van Hoesel et al., 1984, Cancer Res., 44:3698, "Reduced Cardiotoxicity and Nephrotoxicity with Preservation of Antitumor Activity of Doxorubicin Entrapped in Stable Liposomes in the LOU/M Wsi Rat."

Crommelin et al., 1983, Int. J. Pharm., 17(2-3):135, Preparation and Characterization of Doxorubicin-Containing Liposomes. II. Loading Capacity, Long-Term Stability and Doxorubicin-Bilayer Interation Mechanism.

Chen et al., 1956, Anal. Chem., 28:1756, "Microdetermination of Phosphorus".

Singleton et al., 1965, J. A. Oil Chem Soc., 42:53, "Chromatographically Homogeneous Lecithin from Egg Phospholipids".

Tsuganenko et al., 1983, Antibiotiki, 28(8):577, "Preparation and Low-Temperature Preservation of Rifampicin-Containing Liposomes".

FIG. 2 a
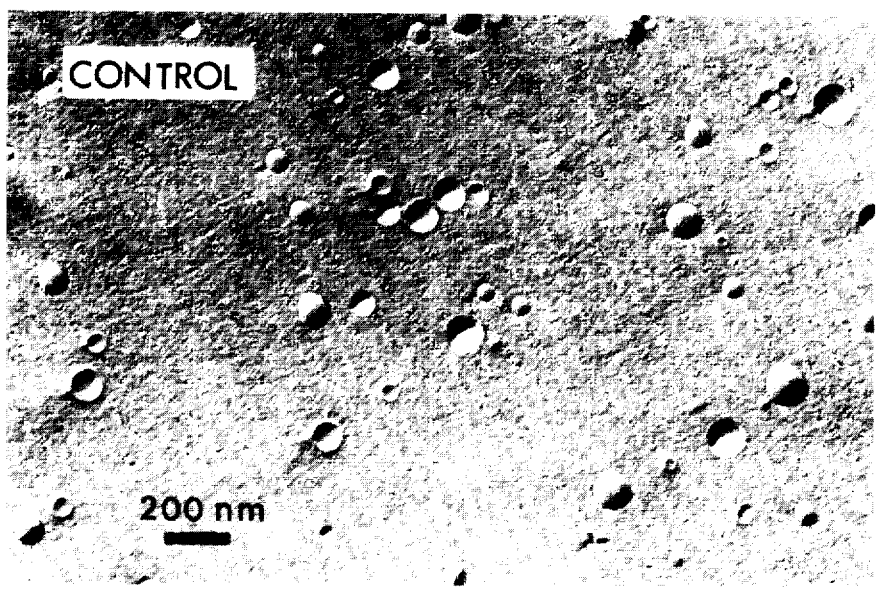
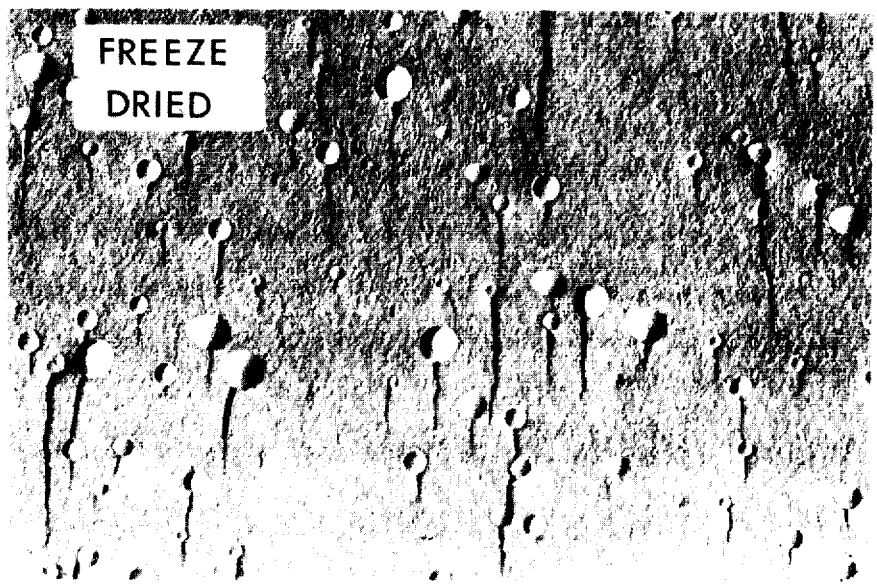
FIG 2 b

FIG. 3 a
FIG. 3 b
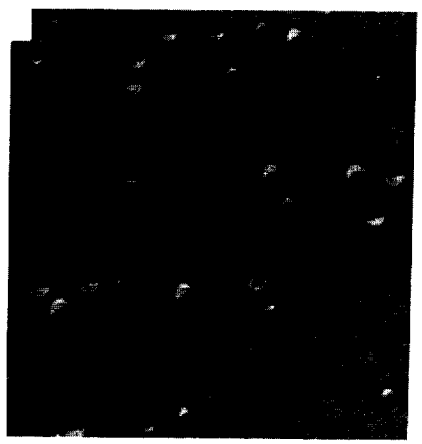
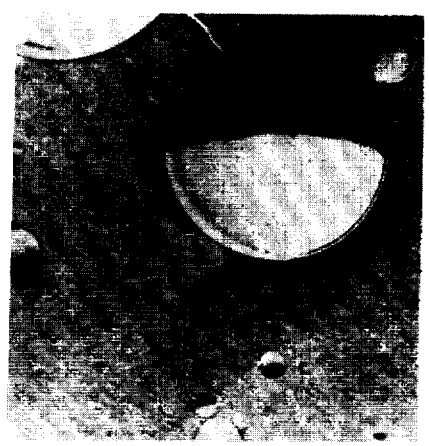
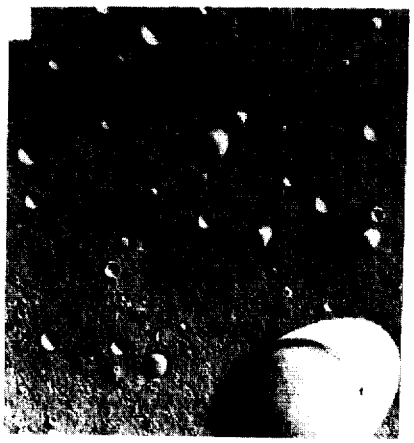
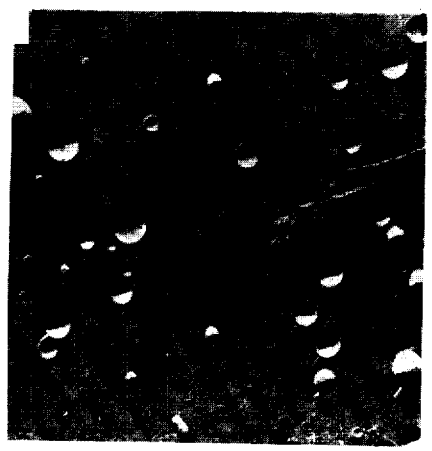
FIG. 3 c
FIG. 3 d

DEHYDRATED LIPOSOMES

CROSS REFERENCE TO RELATED APPLICATIONS

This is a continuation-in-part of copending applications Ser. Nos. 638,809 and 749,161, filed Aug. 8, 1984, and June 26, 1985, respectively, both now abandoned.

BACKGROUND OF THE INVENTION

1. Field of the Invention

This invention relates to liposomes and in particular to dehydrated liposomes which can be stored for extended periods of time and then rehydrated when and where they are to be used.

2. Description of the Prior Art

As is well known in the art, liposomes are closed vesicles having at least one lipid bilayer membrane surrounding an aqueous core. One of the primary uses for liposomes is as carriers for a variety of materials, such as, drugs, cosmetics, diagnostic reagents, bioactive compounds, and the like.

In connection with each of these uses, it is important to be able to store liposomes for long periods of time without substantial leakage from the liposomes of the selected materials they are carrying. More particularly, so as to be useful in commercial settings, liposome preparations must have long enough shelf-lives to allow them to be easily manufactured, shipped, and stored by intermediate and ultimate users under a variety of temperature conditions.

With particular regard to the drug industry, it is also important to be able to provide drug manufacturers with unloaded liposomes which the manufacturers can subsequently load in their own plants with their own drugs. Such a two step or two factory approach (i.e., manufacturing unloaded liposomes in a first plant and then filling them in a second plant) would allow drug manufacturers to purchase a defined commodity, i.e., unloaded liposomes, from suppliers and then use that commodity as an off-the-shelf component of their final product.

As drug manufacturers currently operate their businesses, they strongly prefer to buy defined commodities from suppliers and then assemble the final product in their own plants. In this way, they can personally control the quality of the finished products. Usage of liposome technology by the drug industry would be greatly enhanced if liposomes could also be provided to manufacturers as a defined commodity.

To date, liposome preparations have generally had relatively short shelf-lives. Moreover, there has been no known way to prepare liposomes at one point in time and then fill them with selected materials at a much later point in time. The present invention makes up for these existing shortcomings in the current state of the art.

SUMMARY OF THE INVENTION

In view of the above state of the art, it is an object of the present invention to provide liposome preparations which can be stored for extended periods of time without substantial leakage from the liposomes of internally encapsulated materials.

It is a further object of the present invention to provide liposome preparations which can be dehydrated, stored for extended periods of time while dehydrated, and then rehydrated when and where they are to be used, without losing a substantial portion of their contents during the dehydration, storage and rehydration processes.

It is an additional object of the present invention to provide liposome preparations which can be dehydrated, stored for extended periods of time while dehydrated, rehydrated, and then filled with selected materials.

To achieve these and other objects, the invention, in accordance with one of its aspects, provides liposome preparations which have been dehydrated in the presence of one or more protective sugars. In certain preferred embodiments of the invention, the liposomes are dehydrated with the one or more sugars being present at both the inside and outside surfaces of the liposome membranes. In other preferred embodiments, the sugars are selected from the group consisting of trehalose, maltose, lactose, sucrose, glucose, and dextran, with the most preferred sugars from a performance point of view being trehalose and sucrose.

The dehydration is done under vacuum and can take place either with or without prior freezing of the liposome preparation.

When done without prior freezing, use of the protective sugars can be omitted when (1) the liposomes being dehydrated are of the type which have multiple lipid layers, and (2) the dehydration is done to an end point where there is sufficient water left in the preparation so that a substantial portion of the membranes retain their integrity upon rehydration. Preferably, at least about 2%, and most preferably between about 2% and about 5%, of the original water in the preparation prior to dehydration should remain in the preparation at the end of the dehydration process. In terms of moles of water per mole of lipid in the dehydrated preparation, this corresponds to a water level of preferably at least about 12 moles water/mole lipid, and most preferably between about 12 and about 35 moles water/mole lipid, in the dehydrated preparation.

In accordance with other aspects of the invention, delayed loading of preformed liposomes is achieved by creating a concentration gradient across the liposome membranes of one or more charged species which, under suitable conditions, are capable of passing across those membranes. This concentration gradient is used to load selected charged materials, e.g., drugs, into the liposomes through the creation of a transmembrane potential.

It has been found that liposomes having a concentration gradient across their membranes can be dehydrated in the presence of one or more sugars, as described above and in more detail below, stored in their dehydrated condition, subsequently rehydrated, and the concentration gradient then used to create a transmembrane potential which will load charged materials into the liposomes. Alternatively, the concentration gradient can be created after the liposomes have been dehydrated, stored, and rehydrated. Also, if the dehydration is done without prior freezing of the liposomes and under the conditions described above, the use of protective sugars may be omitted.

The attainment of the foregoing and other objects and advantages of the present invention is described fully below in connection with the description of the preferred embodiments of the invention.

BRIEF DESCRIPTION OF THE DRAWINGS

FIG. 2 shows freeze-fracture electron micrographs of vesicles before (FIG. 2a—Control) and after (FIG. 2b—Freeze Dried) dehydration/rehydration with prior freezing. Egg phosphatidylcholine vesicles were prepared by extruding large multilamellar vesicles through a 100 nm polycarbonate filter. The vesicles were dehydrated in the presence of 250 nM trehalose.

FIG. 3 shows freeze-fracture electron micrographs of egg phosphatidylcholine vesicles before and after dehydration. The vesicles were prepared by extruding large multilamellar vesicles through a 100 nm polycarbonate filter. FIG. 3a shows the vesicles prior to dehydration. FIG. 3b shows the much larger structures obtained by dehydrating and then rehydrating the vesicles without the use of trehalose. FIG. 3c and FIG. 3d shows the vesicles after dehydration and rehydration in the presence of 50 mM and 125 mM trehalose, respectively. The diameter of the large liposome in FIG. 3b is approximately 900 nm and the arrows in the upper right hand corners of the figures indicate the direction of shadowing.

DESCRIPTION OF THE PREFERRED EMBODIMENTS

Figure 1:
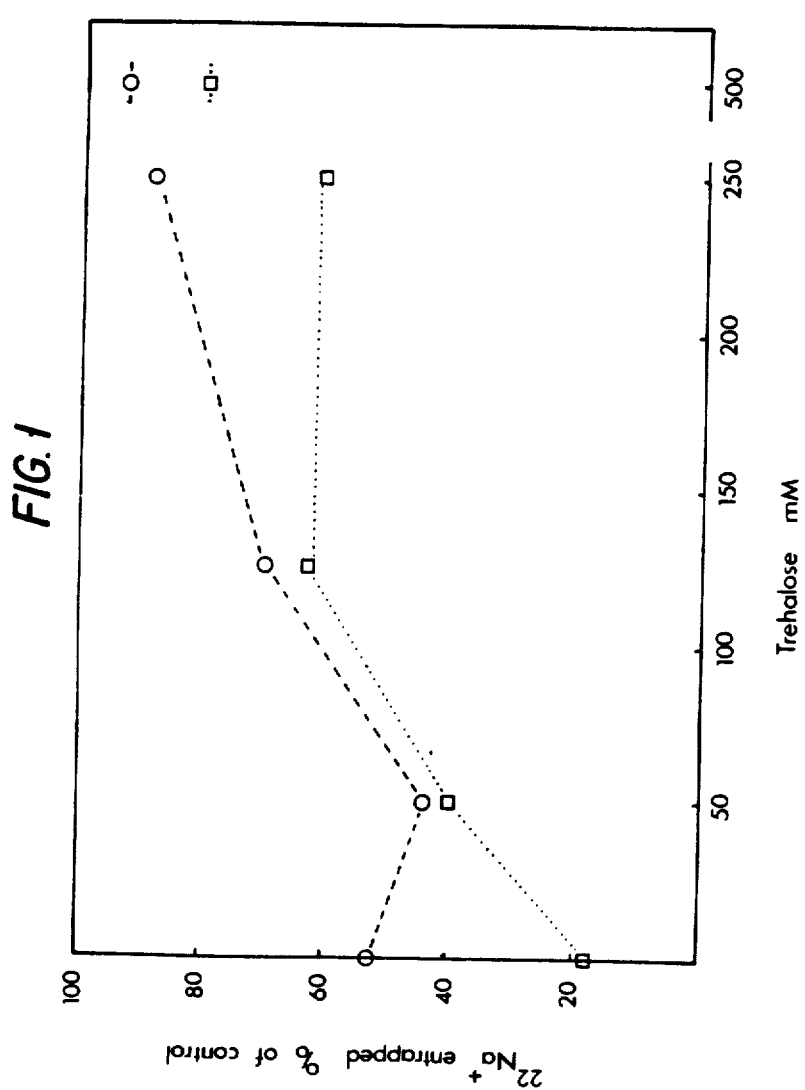
FIG. 1 shows the retention of $^{22}Na^+$ by dehydrated/rehydrated vesicles as a function of trehalose concentration. Large unilamellar vesicles were dried without prior freezing (open circles), or after freezing in liquid nitrogen (open squares).

As described above, the present invention relates to liposomes which can be subjected to long-term storage without substantial loss of their internal contents. The liposomes are stored in a dehydrated state, and the dehydration is performed in the presence of one or more protective sugars. Alternatively, if the liposomes being dehydrated are of the type which have multiple lipid layers and if the dehydration is performed without prior freezing and to an end point where there is sufficient water left in the preparation so that a substantial portion of the membranes retain their integrity upon rehydration, the use of a protective sugar may be omitted.

The liposomes which are to be dehydrated can have a variety of compositions and internal contents, and can be in the form of multilamellar, unilamellar, or other types of liposomes or, more generally, lipid-containing particles, now known or later developed. For example, the lipid-containing particles can be in the form of steroidal liposomes, stable plurilamellar liposomes (SPLVs), monophasic vesicles (MPVs), or lipid matrix carriers (LMCs) of the types disclosed in copending and commonly assigned U.S. patent applications Ser. Nos. 476,496, 521,176, 591,576 and 599,691, filed Mar. 24, 1983, Aug. 8, 1983, Mar. 20, 1984, and Apr. 12, 1984, respectively, the pertinent portions of which are incorporated herein by reference, or can be in the form of freeze and thaw multilamellar vesicles (FATMLVs) of the type described in copending and commonly assigned U.S. patent application Ser. No. 752,423, filed July 5, 1985, and entitled "Multilamellar Liposomes Having Improved Trapping Efficiencies," the pertinent portions of which are also incorporated herein by reference.

The liposomes can be prepared by any of the techniques now known or subsequently developed for preparing liposomes. For example, the liposomes can be formed by the conventional technique for preparing multilamellar liposomes (MLVs), that is, by depositing one or more selected lipids on the inside walls of a suitable vessel by dissolving the lipids in chloroform and then evaporating the chloroform, adding the aqueous solution which is to be encapsulated to the vessel, allowing the aqueous solution to hydrate the lipid, and swirling or vortexing the resulting lipid suspension to produce the desired liposomes.

Alternatively, techniques used for producing large unilamellar liposomes (LUVs), such as, reverse-phase evaporation, infusion procedures, and detergent dilution, can be used to produce the liposomes. A review of these and other methods for producing liposomes can be found in the text *Liposomes,* Marc J. Ostro, ed., Marcel Dekker, Inc., New York, 1983, Chapter 1, the pertinent portions of which are incorporated herein by reference. See also Szoka, Jr., et al., (1980) Ann. Rev. Biophys. Bioengr., 9:467, the pertinent portions of which are also incorporated herein by reference. A particularly preferred method for preparing LUVs is described in commonly assigned and copending U.S. patent application Ser. No. 622,690, filed June 20, 1984, and entitled "Extrusion Technique for Producing Unilamellar Vesicles," the pertinent portions of which are incorporated herein by reference.

As other alternatives, the liposomes can be produced in accordance with the procedures described in U.S. patent applications Ser. Nos. 476,496, 521,176 and 599,691, referred to above, or in accordance with the freeze and thaw procedures described in U.S. patent application Ser. No. 752,423, also referred to above. Also, rather than using liposomes per se, other lipid-containing particles, such as those described in U.S. patent application Ser. No. 591,576, referred to above, can be used in the practice of the present invention. Furthermore, if desired, the liposomes or lipid-containing particles which are to be dehydrated can be given a more uniform size distribution by subjecting them to the process of commonly assigned and copending U.S. patent application Ser. No. 622,502, filed June 20, 1984, and entitled "Liposomes Having Defined Size Distributions," the pertinent portions of which are incorporated herein by reference.

The liposomes are preferably dehydrated using standard freeze-drying equipment or equivalent apparatus, that is, they are preferably dehydrated under reduced pressure. If desired, the liposomes and their surrounding medium can be frozen in liquid nitrogen before being dehydrated. Alternatively, and quite surprisingly, the liposomes can also be dehydrated without prior freezing, by simply being placed under reduced pressure. Dehydration without prior freezing takes longer than dehydration with prior freezing, but the overall process is gentler without the freezing step, and thus there is in general less damage to the liposomes and a corresponding smaller loss of the internal contents of the liposomes. For example, dehydration without prior freezing at room temperature and at a reduced pressure provided by a vacuum pump capable of producing a pressure on the order of 1 mm of mercury can take between approximately 24 and 36 hours, while dehydration with prior freezing under the same conditions can take between approximately 12 and 24 hours.

So that the liposomes will survive the dehydration process without losing a substantial portion of their internal contents, it is important that one or more protective sugars be available to interact with the liposome membranes and keep them intact as the water in the system is removed. A variety of sugars can be used, including such sugars as trehalose, maltose, sucrose, glucose, lactose, and dextran. In general, disaccharide sugars have been found to work better than monosaccharide sugars, with the disaccharide sugars trehalose and sucrose being most effective. Other more complicated sugars can also be used. For example, aminoglycosides, including streptomycin and dihydrostreptomycin, have been found to protect liposomes during dehydration.

The one or more sugars are included as part of either the internal or external media of the liposomes. Most preferably, the sugars are included in both the internal and external media so that they can interact with both the inside and outside surfaces of the liposomes' membranes. Inclusion in the internal medium is accomplished by adding the sugar or sugars to the solute which the liposomes are to encapsulate. Since in most cases this solute also forms the bathing medium for the finished liposomes, inclusion of the sugars in the solute also makes them part of the external medium. Of course, if an external medium other than the original solute is used, e.g., to create a transmembrane potential (see below), the new external medium should also include one or more of the protective sugars.

The amount of sugar to be used depends on the type of sugar used and the characteristics of the liposomes to be protected. As illustrated by Examples 1-5, below, persons skilled in the art can test various sugar types and concentrations to determine which combination works best for a particular liposome preparation. In general, sugar concentrations on the order of 100 mM and above have been found necessary to achieve the highest levels of protection. In terms of moles of membrane phospholipid, millimolar levels on the order of 100 mM correspond to approximately 5 moles of sugar per mole of phospholipid.

In the case of dehydration without prior freezing, if the liposomes being dehydrated are of the type which have multiple lipid layers and if the dehydration is carried out to an end point where there is sufficient water left in the preparation so that a substantial portion of the membranes retain their integrity upon rehydration, the use of one or more protective sugars may be omitted. As discussed above, it has been found preferable if the preparation contains at the end of the dehydration process at least about 2%, and most preferably between about 2% and about 5%, of the original water present in the preparation prior to dehydration.

Once the liposomes have been dehydrated, they can be stored for extended periods of time until they are to be used. The appropriate temperature for storage will depend on the make up of the liposomes and the temperature sensitivity of the encapsulated materials. For example, as is well known in the art, various drug preparations are heat labile, and thus dehydrated liposomes containing such drugs should be stored under refrigerated conditions so that the drugs do not lose their potency. Also, for such drugs, the dehydration process is preferably carried out at reduced temperatures, rather than at room temperature.

When the dehydrated liposomes are to be used, rehydration is accomplished by simply adding an aqueous solution, e.g., distilled water, to the liposomes and allowing them to rehydrate. The liposomes can be resuspended into the aqueous solution by gentle swirling of the solution. The rehydration can be peformed at room temperature or at other temperatures appropriate to the composition of the liposomes and their internal contents.

As discussed above, for certain applications, e.g., drug administration, it is desirable to be able to separate the process of loading liposomes from the process of preparing them. This can be accomplished by creating a transmembrane potential across the membranes of preformed liposomes and using that transmembrane potential to load charged materials, e.g., charged drugs, into the liposomes. The transmembrane potential is generated by creating a concentration gradient for one or more charged species (e.g., $K^+$ and/or $H^+$) across the liposome membranes. The concentration gradient is created by producing liposomes having different internal and external media, i.e., internal and external media having different concentrations of the one or more charged species.

Specifically, liposomes are prepared which encapsulate a first medium having a first concentration of the one or more charged species. For a typical liposome preparation technique (see discussion above), this first medium will surround the liposomes as they are formed, and thus the liposomes' original external medium will have the same composition as the first medium. To create the concentration gradient, the original external medium is replaced by a new external medium having a different concentration of the one or more charged species. The replacement of the external medium can be accomplished by various techniques, such as, by passing the liposome preparation through a gel filtration column, e.g., a Sephadex column, which has been equilibrated with the new medium, or by centrifugation, dialysis, or related techniques.

Depending upon the permeability of the liposome membranes, the full transmembrane potential corresponding to the concentration gradient will either form spontaneously or a permeability enhancing agent, e.g., an ionophore, such as, valinomycin, may have to be added to the bathing medium. (Note that, if desired, the permeability enhancing agent can be removed from the preparation after loading has been completed using chromatography or other techniques). In either case, a transmembrane potential having a magnitude defined by the Nernst equation will appear across the liposomes' membranes. This transmembrane potential will cause charged materials, e.g., charged drugs, to be loaded into the liposomes. Specifically, the transmembrane potential will cause those materials whose charge is opposite to the internal potential of the liposomes (outside ground) to accumulate within the liposomes. Thus, by adding to the external medium the material one wants to load and by choosing the concentration gradient and thus the transmembrane potential to have the appropriate orientation, loading of the liposomes can be accomplished as a separate operation from the creation of the liposomes.

The combination of transmembrane potential loading and liposome dehydration allows for great flexibility in the overall procedure for producing the finished, loaded liposomes. For example, liposomes having the same internal and external media, i.e., no transmembrane potentials, can be prepared, dehydrated, stored, rehydrated, and then the external medium can be replaced with a new medium having a composition which will generate transmembrane potentials, and the transmembrane potentials used to load the liposomes. Alternatively, liposomes having internal and external media which will produce transmembrane potentials can be prepared, dehydrated, stored, rehydrated, and then loaded using the transmembrane potentials.

In either case, when in their dehydrated state, the unloaded liposomes can be stored, shipped and otherwise easily handled. In particular, the dehydrated, unloaded liposomes are exactly the type of defined commodity which drug manufacturers prefer to purchase and thus satisfy the long felt need for a liposome product of this type (see discussion above).

A particularly important application of these transmembrane potential loading and/or liposome dehydration procedures is in the area of the administration of antineoplastic agents, such as, adriamycin (see Examples 1 and 6, below). A further discussion of these applications can be found in copending and commonly assigned U.S. patent application Ser. No. 749,161, filed June 26, 1985, and entitled "Encapsulation of Antineoplastic Agents in Liposomes," the pertinent portions of which are incorporated herein by reference.

Without intending to limit it in any manner, the present invention will be more fully described by the following examples. The materials and methods which are common to the various examples are as follows.

MATERIALS AND METHODS

Materials

Egg phosphatidylcholine (EPC) was isolated employing standard procedures (see, for example, Singleton, et al., (1965) Journal of the American Oil Chemical Society, 42:53) and was more than 99% pure as determined by TLC. Trehalose, maltose, sucrose and glucose were obtained from the Sigma Chemical Company (St. Louis, Mo.), while lactose was purchased from Fisher Scientific Company (Fairlawn, N.J.). $^{22}Na^+$, $^3H$-inulin, $^3H$-tetraphenylphosphonium bromide and $^3H-H_2O$ were obtained from New England Nuclear (Lachine, Quebec). Adriamycin was obtained from Adria Laboratory (Mississauga, Ontario).

Vesicle Preparation

Vesicles were prepared using the extrusion techniques described in U.S. patent applications Ser. Nos. 622,690 and 622,502, referred to above. A complete description of the techniques used appears in those applications and is incorporated herein by reference. Vesicles prepared by these techniques will be referred to herein as ETVs, i.e., Extrusion Technique Vesicles.

Briefly, 80 umoles of egg phosphatidylcholine was hydrated with 2 ml of 150 mM NaCl, 20 mM HEPES (pH 7.4) containing the indicated concentration of trehalose or other sugars. In those cases where the amount of residual water present after dehydration was determined, $^3H$-water (30 uCi) was added to the HEPES buffer/sugar solution. $^{22}Na^+$ (5 uCi) or $^3H$-inulin (5 uCi; specific activity 409 mCi/g) were added to the dry lipid prior to hydration.

The mixture was dispersed by vortexing and then passed ten times through two stacked polycarbonate filters of 100 nm pore size (Nuclepore, Inc., Pleasanton, CA) using a pressure of 250 psi. In those cases where a freeze-thaw procedure was utilized, the vesicles were prepared as above, freeze-thawed once using liquid nitrogen, and then again repeatedly passed through the stacked filters.

Unencapsulated $^{22}Na^+$ or $^3H$-inulin was removed by passing the vesicles through a column (1.4×10 cm) of either Sephadex G-50 (fine) for removal of $^{22}Na^+$ or Ultragel AcA 34 for removal of $^3H$-inulin. This procedure generally diluted the phospholipid content of the sample by approximately 50% to give a concentration of about 20 umoles phospholipid per mililiter.

Dehydration

Samples (1 ml) were dried in 10 ml Kimex tubes at room temperature under high vacuum using a Virtis Freeze Drier (Gardiner, N.Y.). In some cases, the samples were frozen in liquid nitrogen prior to dehydration. In either case, the reduced pressure dehydration process was carried out for approximately 24 hours.

Rehydration

Following dehydration and storage for periods ranging from 1 to 7 days, the samples were rehydrated with distilled water (900 ul) and the vesicles dispersed by gentle vortexing. The amount of entrapped $^{22}Na^+$, $^3H$-inulin or adriamycin remaining within the vesicles was measured using the techniques described below (see "Assays") after passage of 100 ul aliquots of the vesicle suspension over columns (1 ml) of Sephadex G-50 (fine) or Ultragel AcA 34, equilibrated with the same solution in which the vesicles were suspended, to remove any untrapped material (see U.S. patent application Ser. No. 622,690 for further details). Since the columns tend to trap a small percentage of the liposomes applied thereto, the values reported below for the amounts of encapsulated material retained after the dehydration/rehydration process are somewhat lower than the levels actually achieved by the procedures of the present invention.

Freeze Fracture Electron Microscopy

Samples for freeze-fracture contained 25% glycerol and were fractured and replicated following the procedures described in Madden, T. D., Hope, M. J. and Cullis, P. R. (1983) Biochemistry 22, 1970–1974, using a Balzers freeze-fracture apparatus. Replicas were visualized on a Phillips 400 electron microscope.

Quasi-Elastic Light Scattering Measurements

Vesicles were sized employing a Nicomp 200 Laser Particle Sizer (Nicomp Instrument, Goleta, Calif.) operating at 632.8 nm and 5 mW.

Assays

Phospholipids were quantified by determination of inorganic phosphorus as described by Chen, et al., (1956) Anal. Chem. 28:1756. Adriamycin uptake was measured following solubilization of vesicles in 0.5% Triton X-100 from its absorbance at 480 nm. $^3H$-inulin, $^3H-H_2O$ and $^3$-tetraphenylphosphonium were counted in a Phillips PW 4700 liquid scintillation counter, while $^{22}Na^+$ was quantified by gamma counting on a Beckman Gamma 800.

EXAMPLE 1

Dehydration of Liposomes Using the Protective Sugar Trehalose

This example illustrates the ability of the sugar trehalose to protect liposomes from substantial loss of their internal contents during dehydration and subsequent rehydration. Experiments demonstrating high retention levels for $^{22}Na^+$, $^3 H$-inulin, and adriamycin were performed. The results are shown in FIGS. 1-4 and Table 1.

In particular, egg phosphatidylcholine ETVs were prepared as described above using solute solutions containing $^{22}Na^+$ and various concentrations of trehalose. The ETVs were dehydrated with or without prior freezing in liquid nitrogen, rehydrated and assayed as described above. The results are shown in FIG. 1.

As shown in that figure, the amount of $^{22}Na^+$ retained in the vesicles after rehydration depends on the trehalose concentration, with up to 90% of the sodium being retained at the highest concentration of trehalose tested (500 mM). As also shown in that figure, vesicles dehydrated without prior freezing retain more of their contents than those frozen in liquid nitrogen. That is, dehydration without freezing is overall a gentler process than dehydration with freezing.

The ability of trehalose to protect liposomes during dehydration/rehydration is further illustrated by the freeze-fracture electron micrographs of FIG. 2 which shows liposomes before (FIG. 2a—Control) and after (FIG. 2b—Freeze Dried) dehydration/rehydration with prior freezing. The trehalose concentration in this case was 250 mM. As can be seen in this figure, the appearance of the liposome population is essentially unchanged by the dehydration/rehydration process, that is, the trehalose successfully protects the liposomes during this process.

Experiments performed without any trehalose in the solute solution gave a milky suspension upon rehydration in contrast to the opulescent appearance of the original sample. In addition, recovery of vesicles from the 1 ml Sephadex columns used to strip unencapsulated $^{22}Na^+$ was low (less than 10%), indicating that the liposomes had fused to form larger structures.

FIG. 3 shows the effects of varying the trehalose concentration. FIG. 3a shows the liposomes prior to drying, while FIG. 3b shows them after drying and rehydration in the absence of trehalose. As is evident from these figures, the original vesicles are small and uniform in size, while the dehydrated/rehydrated vesicles are in general much larger.

FIG. 3c and FIG. 3d show liposomes which have been dried and rehydrated in the presence of 50 mM and 125 mM trehalose, respectively. As shown by these figures, vesicles dried in the presence of 50 mM trehalose and then rehydrated are generally the same size as prior to dehydration, but a small fraction of layer structures are also observed. At trehalose concentrations of 125 mM or greater, there is not discernible structural difference between vesicles before and after dehydration and rehydration.

To verify that vesicles dehydrated in the presence of trehalose retain their contents and do not simply reencapsulate label upon rehydration, vesicles were prepared in 250 mM trehalose, and $^{22}Na^+$ was then added to the external medium. Following dehydration and rehydration, aliquots of the suspension were passed down 1 ml Sephadex columns as described in Materials and Methods above. Of the available $^{22}Na^+$, less than 0.02% was sequestered by the rehydrated vesicles, confirming that they do not encapsulate solute in the external medium upon rehydration.

Figure 4:
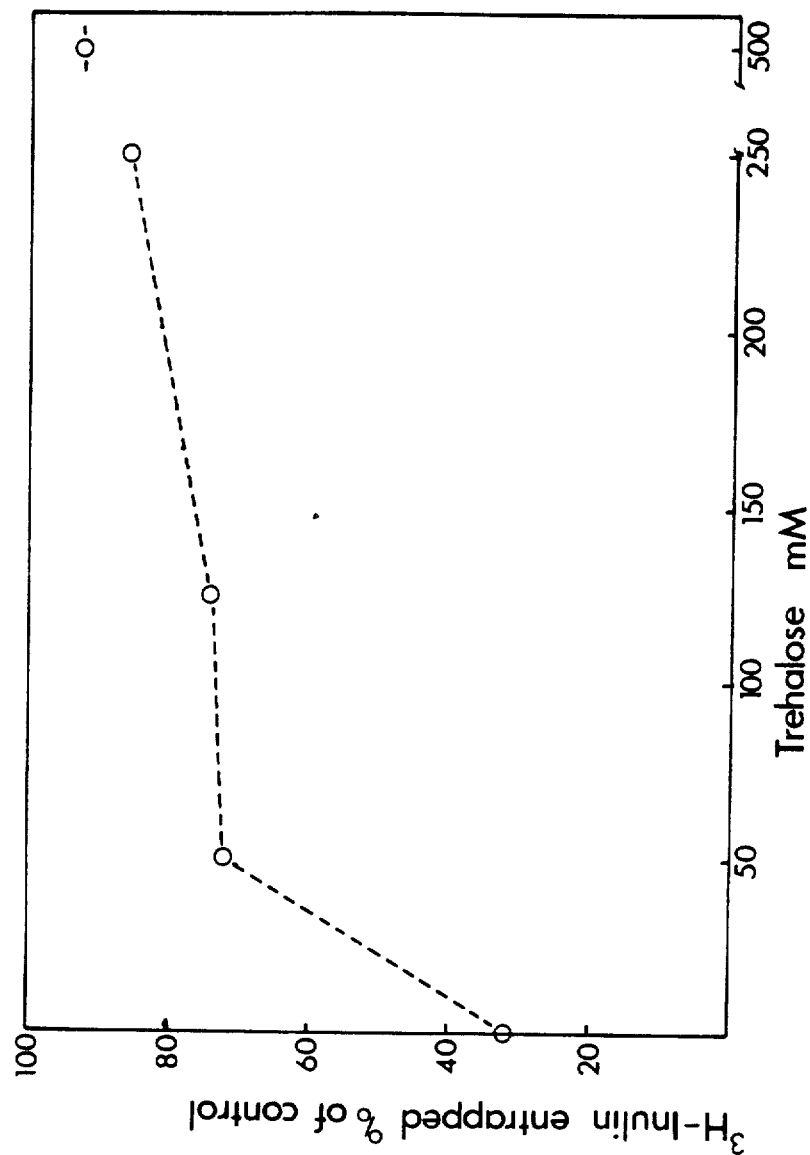
FIG. 4 shows the retention of $^3H$-inulin as a function of trehalose concentration. Large unilamellar vesicles containing entrapped $^3H$-inulin were dried under high vacuum without prior freezing.

The ability of dehydrated ETVs to retain inulin (molecular weight 5000) is shown as a function of trehalose concentration in FIG. 4. A comparison of that figure with FIG. 1, reveals that for the same trehalose concentration, more of the high molecular weight inulin is retained than the low molecular weight sodium. However, at the higher trehalose concentrations, the difference is quite small, suggesting that the small amount of each label lost may be the result of vesicle rupture rather than permeability changes.

The ability of ETVs to retain the antitumor drug adriamycin when dehydrated in the presence of trehalose is shown in Table 1. The data presented in this table was obtained as follows: Egg phosphatidylcholine ETVs were prepared as described above using a solute solution (169 mM KGlu, 20 mM HEPES (pH 7.4), 40 umol lipid/ml) containing 250 mM trehalose. Subsequently, the external potassium buffer was exchanged for a sodium buffer (150 mM NaCl, 20 mM HEPES (pH 7.4), 250 mM trehalose). Adriamycin (200 nmol/umol lipid) was added, along with valinomycin (0.5 ug/umol lipid) to induce a membrane potential. After a 2 hour incubation, unencapsulated adriamycin was removed by passing the vesicles through a column of Sephadex G-50 equilibrated with the trehalose-containing sodium buffer described above. The ETVs were dehydrated for 24 hours without prior freezing and then rehydrated as described above.

The amounts of entrapped adriamycin in the vesicles both before and after dehydration/rehydration, as well as the rate of drug leakage from the vesicles, were measured by first passing 100 ul aliquots of the vesicle suspension over columns (1 ml) of Sephadex G-50 to remove any untrapped material (see U.S. patent application Ser. No. 622,690 for further details). Trapped adriamycin was then quantitated by mixing an aliquot of the vesicle suspension with 0.5% Triton X-100 (which disrupted the vesicles and released the trapped drug) and monitoring the absorbance at 480 nm employing a Pye Unicam SP8-200 spectrophotometer. Since the columns tend to trap a small percentage of the liposomes applied thereto, the measured values for the amounts of encapsulated material retained after the dehydration/rehydration process are somewhat lower than the levels actually received.

The results of these experiments are shown in Table 1. As shown therein, more than 90% of the drug is retained following dehydration and rehydration, i.e. the same levels as those achieved with $^{22}Na^+$ and $^3H$-inulin. Moreover, the rate of leakage of adriamycin from the rehydrated vesicles is comparable to the rate observed with vesicles which have not been dehydrated (see Bally, et al., (1985), *Biochim. Biophys. Acta.*, 812:66).

As clearly demonstrated by this Example, the sugar trehalose is capable of protecting liposomes during dehydration and subsequent rehydration so that more than 90% of the material encapsulated within the liposomes is still retained therein after rehydration.

EXAMPLE 2

EXPOSURE OF BOTH THE INSIDE AND OUTSIDE SURFACES OF LIPOSOME MEMBRANES TO A PROTECTIVE SUGAR

This example illustrates the enhanced protective effect achieved by having a protective sugar (trehalose) in contact with both the internal and external surfaces of the liposome membranes.

ETVs were prepared with trehalose on both sides of the membrane (by including trehalose in the solute solution used to form the vesicles) or only on the outside of the membrane (by excluding trehalose from the solute solution and adding it to the external medium after the vesicles had been formed). The vesicles were dehydrated and at various points in time, up to 72 hours, samples were rehydrated and the level of $^{22}Na^+$ retained determined. The results are shown in Table 2, together with values for the amount of residual water present in the samples following description.

As shown in this table, maximum protection is achieved when the protective sugar is present on both membrane surfaces. Also, when only the external surface is exposed to the protective sugar, the amount of structural damage which the vesicles undergo is related to the amount of residual water present in samples.

EXAMPLE 3

Effects of Vesicle Size And Salt Concentration

This example describes the effects of various vesicle sizes and salt concentrations on the ability of trehalose to protect vesicles during dehydration and rehydration.

ETVs of various sizes were produced using polycarbonate filters having pore sizes ranging from 50 nm to 800 nm. The ETVs were subjected to a freeze-thaw cycle as described above in "Materials and Methods." The mean diameters of the resulting vesicles as measured by quasi-elastic light scattering are given in Table 3.

As shown by the data in Table 3, the ability to retain $^{22}Na^+$ is relatively insensitive to vesicle size. Moreover, since the larger vesicles contained some multilamellar structure, this data illustrates that sugar protection is achieved for multilamellar vesicles. Although the data in Table 3 indicates that the most stable vesicles would appear to be those with a mean diameter of about 170 nm, the multilamellar structure of the larger vesicles makes a rigorous comparison difficult.

Figure 5:
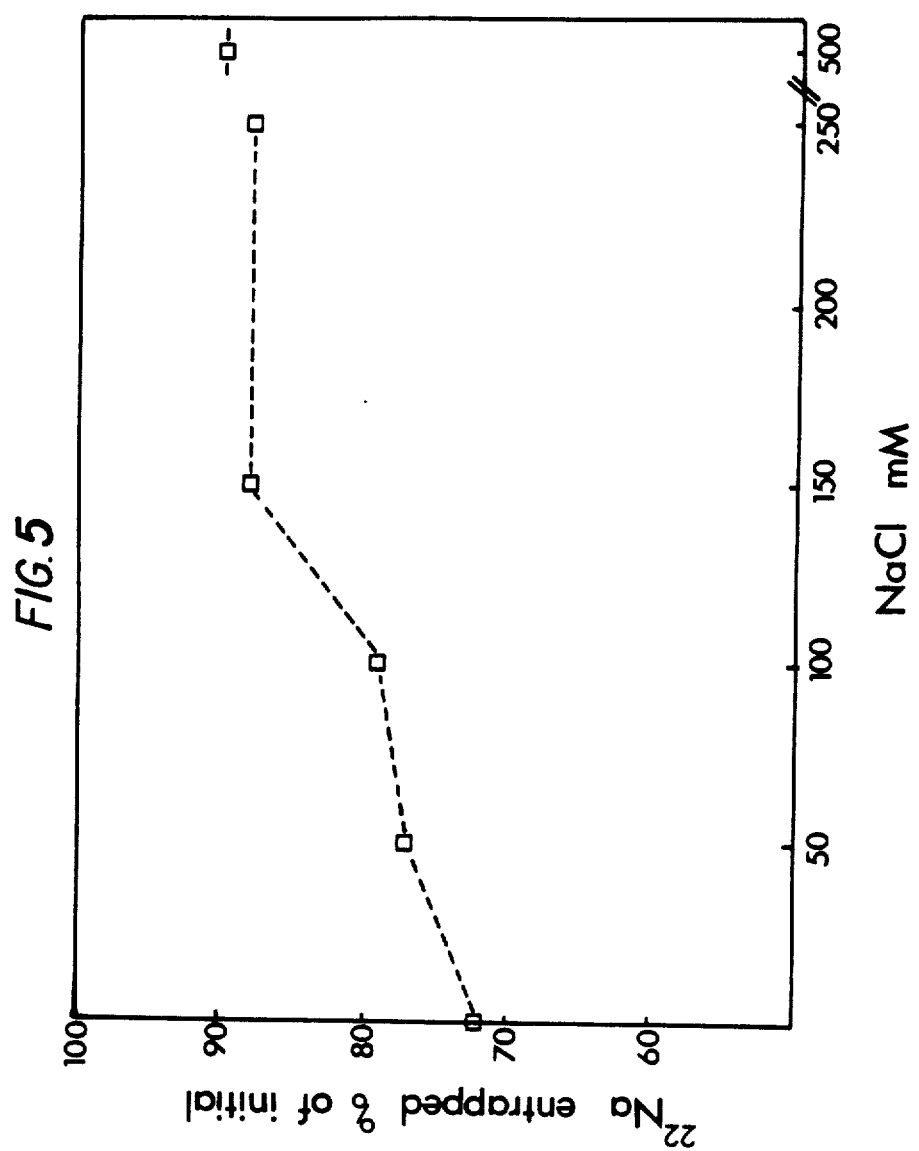
FIG. 5 shows the influence of sodium chloride concentration on the amount of $^{22}Na^+$ retained by dehydrated/rehydrated vesicles. The vesicles were dried in the presence of 250 mM trehalose under high vacuum for 24 hours.

The effects of varying the salt concentration of the internal and external media for a fixed trehalose concentration is shown in FIG. 5. As shown therein, there is a small but significant increase in the amount of $^{22}Na^+$ retained in the vesicles with higher salt concentrations.

EXAMPLE 4

Relative Ability of Trehalose and Other Sugars to Protect Vesicles during Dehydration This example illustrates the relative ability of trehalose and other sugars to protect vesicles during dehydration.

Vesicles were prepared in 500 mM trehalose, maltose, lactose, sucrose, and glucose and the amount of $^{22}Na^+$ retained by the vesicle following dehydration and rehydration determined. As shown in Table 4, trehalose and sucrose were the most effective followed by maltose, glucose and lactose.

EXAMPLE 5

Dehydration of Liposomes Using the Protective Sugar Streptomycin

This example illustrates the ability of the sugar streptomycin to protect liposomes from substantial loss of their internal contents during dehydration and subsequent rehydration. Experiments demonstrating high retention of $^3H$-inulin were performed.

In particular, egg phosphatidylcholine monophasic vesicles (MPVs) were prepared as described in copending and commonly assigned U.S. patent application Ser. No. 521,176, filed Aug. 8, 1983, and entitled "Lipid Vesicles Prepared in a Monophase." A complete description of the technique used in this example appears in that application and is incorporated herein by reference.

Briefly, 127 umoles of egg phosphatidylcholine were used in the vesicle preparation. $^3H$-inulin and various concentrations of streptomycin were added to phosphate buffered saline (PBS) lacking divalent cations (pH 7.3), and MPVs were formed. The MPVs were dehydrated with prior freezing, rehydrated in PBS and assayed for retained $^3$H-inulin as described above. The results are shown in Table 5.

As shown in this table, the amount of $^3$H-inulin retained in the vesicles after rehydration depends on the streptomycin concentration, with up to 86% of the inulin being retained at the highest concentration of streptomycin tested (568 mM).

The ability of dihydrostreptomycin to protect liposomes during dehydration/rehydration was also tested following essentially the same protocol as that used with streptomycin except that washing of the MPVs was done with PBS lacking dihydrostreptomycin so that dihydrostreptomycin was only included as part of the internal contents of the finished liposomes. In this case a retention level of 63% was observed for a dihydrostreptomycin concentration level of 565 mM.

EXAMPLE 6

Loading of Rehydrated Liposomes Using Transmembrane Potentals

This example illustrates: (1) that liposomes having a concentration gradient across their membranes can be dehydrated in the presence of a protective sugar and rehydrated without loss of the concentration gradient; and (2) that after rehydration, the concentration gradient can be used to load a charged material (the drug adriamycin) into the liposomes.

Vesicles having a $Na^+-K^+$ chemical gradient across their membranes were prepared by forming ETVs in a potassium glutamate buffer (169 mM potassium glutamate, 250 mM trehalose, 20 mM HEPES, pH 7.4), and then replacing the external buffer with a NaCl buffer (150 mM NaCl, 250 mM trehalose, 20 mM HEPES, pH 7.4) by passing the vesicles through a Sephadex G-50 (fine) column (1.4×10 cm) which had been pre-equilibrated with the NaCl solution. Where employed, valinomycin (Sigma, St. Louis, Mo.) was added in ethanol to a concentration of 0.5 ug/umole phospholipid.

Similarly, transmembrane pH gradients (interior acid) were formed by preparing the liposomes in a buffer with low pH (135 mM glutamic acid, 250 mM trehalose, brought to pH 5.5 by the addition of potassium hydroxide) which was then exchanged with a high pH buffer (125 mM glutamic acid, 30 mM NaCl, 250 mM trehalose, brought to pH 7.5 by the addition of potassium hydroxide) on a Sephadex G-50 (fine) column. Where used, the proton ionophore CCCP was added to a final concentration of 20 uM.

Transmembrane potentials were measured by determining the distribution of the lipophilic cation $^3$H-tetraphenylphosphonium bromide ($^3$H-TPPB, NEN, Canada). Specifically, 1 uCi of $^3$H-TPPB in 1 ul ethanol was added to a 1–2 ml sample of the ETV dispersion and the mixture was incubated at 20° C. for 20 minutes. An aliquot (100 ul) was withdrawn and the untrapped $^3$—TPP$^+$ was removed by loading the aliquot onto a Sephadex G-50 column packed in a 1 ml disposable syringe, and then centrifuging the column at 500 g for 3 minutes to elute the vesicles. The trapped $^3$H-TPP$^+$ was determined by liquid scintillation counting, and the phospholipid determined by phosphate assay.

Using trapped volume values (ul per umol of phospholipid) for the ETVs determined by measuring the amount of $^{22}$Na or $^3$H-inulin captured in the ETVs by the ETV process, the concentrations of $^3$H—TPP$^+$ inside [$^3$H—TPP$^+$]$_i$ and outside [$^3$H—TPP$^+$]$_o$ the vesicles were calculated, from which the transmembrane potential (V$_m$) was calculated using the Nernst equation:

$$V_m = -59 \log [^3H-TPP^+]_i/[^3H-TPP^+]_o.$$

Figure 6:
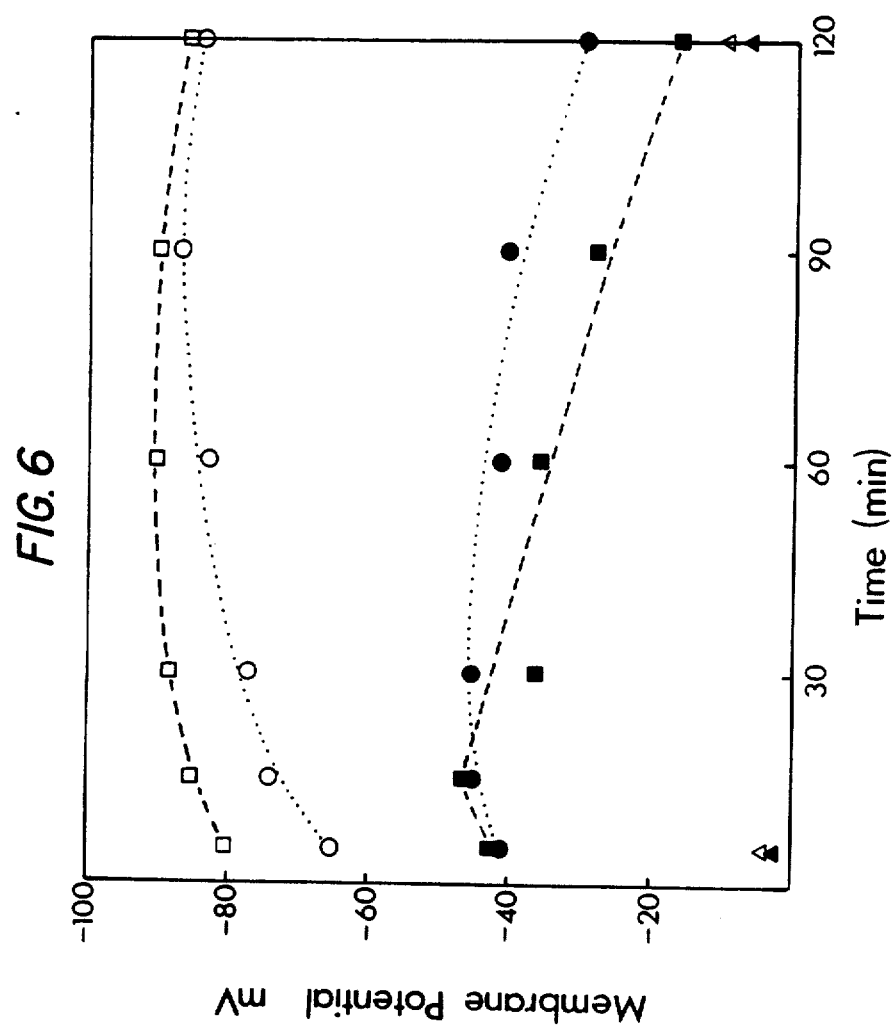
FIG. 6 shows the transmembrane potentials generated by a pH gradient for control vesicles (squares) and dehydrated/rehydrated vesicles (circles). Vesicles with a pre-existing proton gradient were maintained at 4° C. for 24 hours (control) or dehydrated in the presence of 250 mM trehalose under high vacuum for the same period of time. The potential observed in the vesicles upon rehydration was determined in the absence of CCCP (open circles and squares), or with 20 uM CCCP present (solid circles and squares), using the probe $^3H$-tetraphenylphosphonium bromide. The transmembrane potentials observed in vesicles without a pH gradient in the presence and absence of CCCP is shown by the solid and open triangles, respectively.
Figure 7:
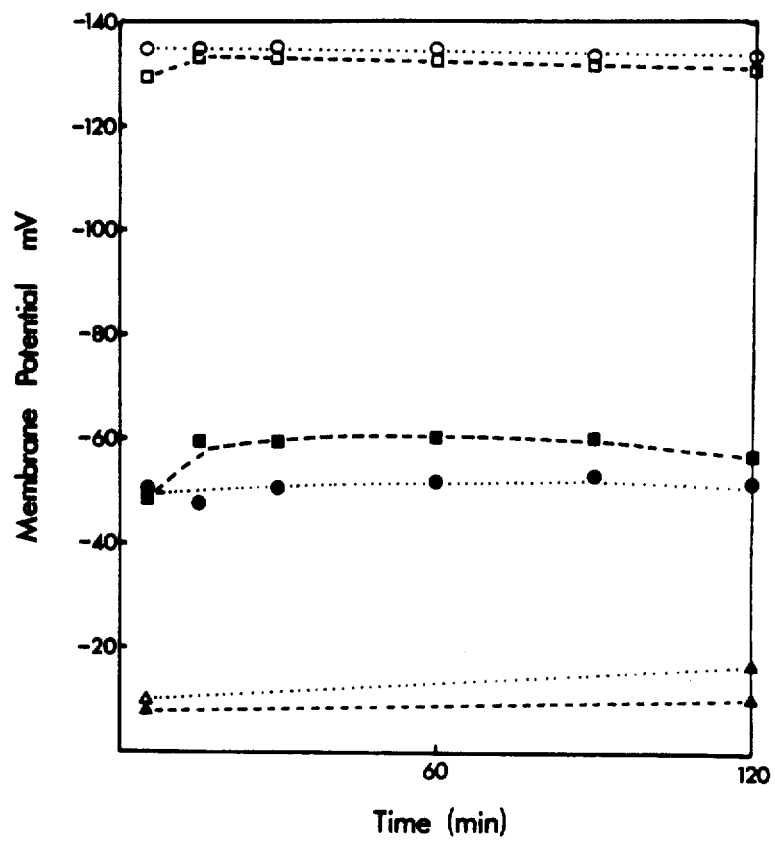
FIG. 7 shows the transmembrane potentials generated by a $Na^+/K^+$ chemical gradient for control vesicles (squares) and dehydrated/rehydrated vesicles (circles). Vesicles with a pre-existing $Na^+/K^+$ gradient were maintained at 4° C. for 24 hours (control) or dehydrated in the presence of 250 mM trehalose under high vacuum for the same period of time. The potential observed in the vesicles upon rehydration was determined in the absence of valinomycin (solid circles and squares), or with 0.5 ug/umole phospholipid valinomycin present (open circles and squares), using the probe $^3H$-tetraphenylphosphonium bromide. The transmembrane potentials observed in vesicles having potassium glutamate on both sides of the membrane in the presence and absence of valinomycin is shown by the open and solid triangles, respectively.

Both the Na$^+$/K$^+$ and the pH gradient vesicles were dehydrated under high vacuum for 24 hours and then rehydrated. Control vesicles were kept at 4° C. for 24 hours. Following drying and rehydration, the transmembrane potentials exhibited by these vesicles in the presence and absence of ionophores were compared to the transmission potentials generated by the controls, also in the presence and absence of ionophores. The results are shown in FIGS. 6 (pH) and 7 (Na$^+$/K$^+$).

As can be seen from these figures, the transmembrane potentials exhibited by the vesicles which had been dehydrated and then rehydrated are essentially identical to those exhibited by the controls. The only apparent different is that in the case of the pH gradient vesicles, the transmembrane potentials for the dehydrated/rehydrated vesicles develop somewhat slower than the transmembrane potentials for the control vesicles.

The ability of the Na$^+$/K$^+$ vesicles to accumulate adriamycin after dehydration and rehydration was tested in the presence and absence of the ionophore valinomycin, and compared with the accumulation exibited by the control vesicles, i.e., the vesicles which had been stored at 4° C. for 24 hours rather than being dehydrated for 24 hours. Sufficient adriamycin was added to the vesicles' external medium to produce a final concentration of 0.2 moles adriamycin per mole of phospholipid.

Figure 8:
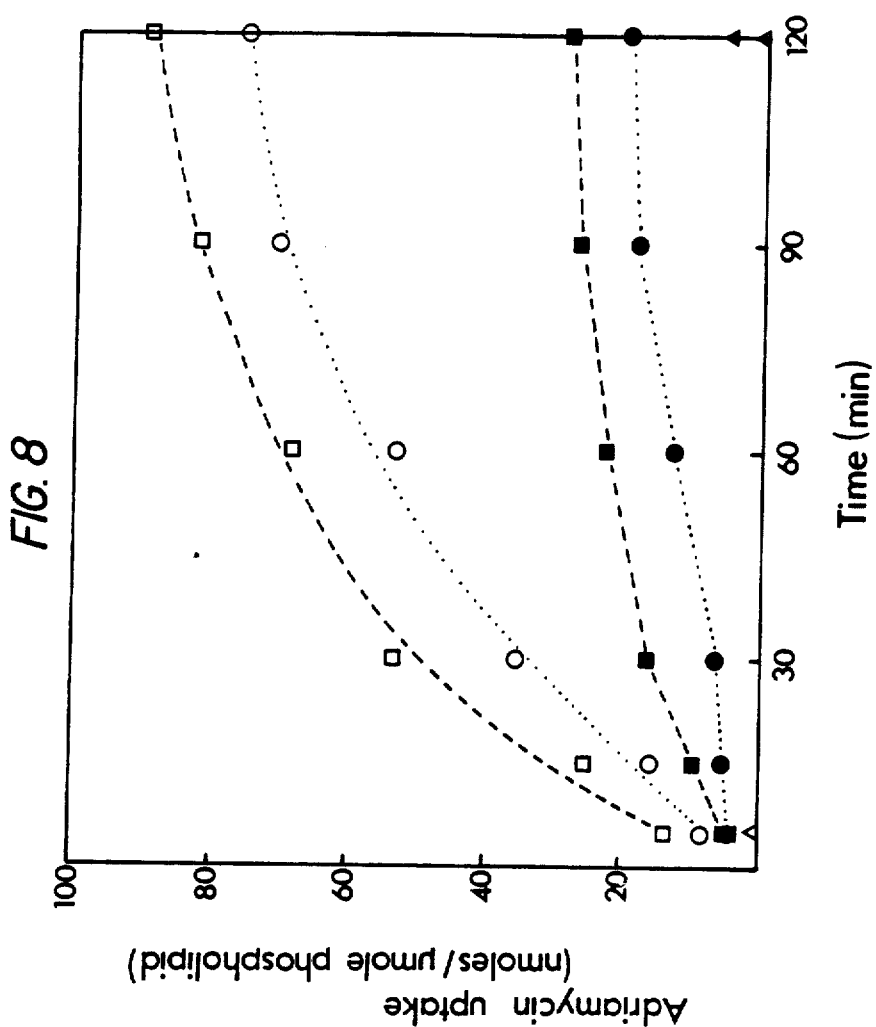
FIG. 8 illustrates the use of a transmembrane potential to load adriamycin into previously dried vesicles. Vesicles with a pre-existing $Na^+/K^+$ gradient were dehydrated for 24 hours in the presence of 250 mM trehalose. Following rehydration the ability of the vesicles to accumulate adriamycin in the presence (open circles), or absence (solid circles) of valinomycin (0.5 ug/umole phospholipid) was measured. Control vesicles maintained at 4° C. for the same period were also tested in the presence (open squares) or absence (solid squares) of valinomycin.

The results of these tests are shown in FIG. 8. As can be seen therein, the dehydrated/rehydrated vesicles accumulate adriamycin essentially at the same rate and to the same extent as the control vesicles.

Although not wishing to be bound by any particular theory of operation, one of the mechanisms involved in the observed uptake of adriamycin in response to Na$^+$/K$^+$ gradients may involve the pH gradients which are automatically generated in response to such gradients due to the permeability of liposome membranes to H$^+$ ions. In accordance with this mechanism, adriamycin passes through the membrane in an uncharged state, with its internal and external concentrations being a function of the internal and external H$^+$ ion concentrations, the internal concentration being high when the internal H$^+$ concentration is high, and vice versa.

In sum, this example demonstrates that delayed loading of vesicles can be accomplished through the combination of concentration gradients and the dehydration/rehydration process.

EXAMPLE 7

Dehydration of Liposomes Having Multiple Lipid Layers Without Prior Freezing and Without the Use of a Protective Sugar This example illustrates that liposomes having multiple lipid layers will retain a substantial portion of their internal contents during dehydration and subsequent rehydration, even without the use of a protective sugar, provided that the dehydration is performed without prior freezing of the liposomes and provided that the dehydration is performed to an end point where there is sufficient water left in the preparation so that a substantial portion of the membranes retain their integrity upon rehydration.

The experiments were performed using the following types of liposomes, all of which include multiple lipid layers: multilamellar liposomes (MLVs), stable plurilamellar liposomes (SPLVs), and monophasic vesicles (MPVs). A detailed description of suitable techniques for producing SPLVs and MPVs appears in copending and commonly assigned U.S. patent applications Ser. Nos. 476,496 and 521,176, respectively, the pertinent portions of which are incorporated herein by reference. Descriptions of methods for preparing MLVs can be found throughout the literature, including, for example, the *Liposome* text (Marc. J. Ostro, ed., 1983) and the Szoka, Jr., et al. reference (Ann. Rev. Biophys. Bioengr., 1980), referred to above, the pertinent portions of which are also included herein by reference.

The materials and experimental protocol used were as follows. All three types of liposomes were made with egg phosphatidylcholine (EPC) obtained from Sigma Chemical Company and with Hepes buffer with and without trehalose (i.e., 20 mM Hepes, 150 mM NaCl, pH 7.4—Buffer 0; or 20 mM Hepes, 150 mM NaCl, 250 mM trehalose, pH 7.4—Buffer 250). $^{51}CrO_4^=$ (New England Nuclear) in normal saline was used as the tracer. 0.01 ml of the tracer produced a cpm level of approximately 500,000.

For each of the three types of liposomes, the EPC was dissolved in $CHCl_3$ (100 mg/ml) and 3.14 ml of the resulting solution was deposited on the sides of a glass, round bottom flask using a Rotovap evaporator. To make SPLVs, the lipid was redissolved in ether (10 ml) to which was added 0.5 ml of either Buffer 0 or Buffer 250 which included 0.01 ml of the tracer solution. The ether was blown off under a stream of nitrogen while sonicating in a bath sonicator. 4.5 ml of Buffer 0 or Buffer 250 was then added, producing a final lipid concentration of 62.8 mg/ml.

To make MPVs, the lipid was redissolved in 100% ethanol (10 ml) to which was added 0.5 ml of either Buffer 0 or Buffer 250 which included 0.01 ml of the tracer solution. The ethanol was evaporated off at 55°–60° C. using a Rotovap evaporator. 4.5 ml of Buffer 0 or Buffer 250 was then added, producing a final lipid concentration of 62.8 mg/ml.

MLVs were made by adding 5.0 ml of Buffer 0 or Buffer 250 to the round bottom flask and then vortexing the samples with glass beads for approximately 5 minutes. The buffers included 0.01 ml of the tracer solution. As with the SPLVs and the MPVs, the final lipid concentration was 62.8 mg/ml.

Once all six liposomes samples had been prepared (one with and one without trehalose for each of the three types of liposomes), they were removed from the round bottom flasks by vortexing for approximately 5 minutes, and each sample was placed in a dialysis bag made of Thomas 12,000 M.W. dialysis tubing. The radioactivity of each bag was counted and the bags were then dialyzed against 500 ml of Buffer 0 or Buffer 250, as appropriate, until a stable count was reached indicating that the tracer had been removed from the external medium surrounding the liposomes. Dialysis for approximately 24 hours was found sufficient to reach a stable count.

Without prior freezing, 1.0 milliliter of each sample was dried for 24 hours in a 10 ml Kimex tube at room temperature under high vacuum using a Virtis Freeze Drier (Gardiner, N.Y.). As the results presented below for the liposome preparations which did not include trehalose show, dehydration for this period of time and under these conditions resulted in dehydrated preparations which included sufficient residual water so that a substantial portion of the liposome membranes retained their integrity upon rehydration even though a protective sugar was not used.

After dehydration, the liposomes were placed in 0.9 ml of distilled water and slowly rehydrated with gentle swirling or vortexing, as necessary.

The rehydrated liposomes were transferred to dialysis bags of the type described above and their radioactivity measured. The bags were then dialyzed against Buffer 0 or Buffer 250, as appropriate, for approximately 18 hours and their radioactivity measured again. The amount of radioactivity retained by the liposomes after dialysis was used as a measure of the amount of internal contents which the liposomes were able to retain through the dehydration/rehydration process. As a control, 1.0 milliliter of each sample was placed in a 10 ml Kimex tube, held at room temperature without drying for 24 hours, placed in a dialysis bag, measured for radioactivity, dialyzed against the appropriate buffer, and then remeasured for radioactivity.

The results of these experiments were as follows, where the percentages given are the counts per minute after dialysis relative to the counts per minute before dialysis and where the numbers in parentheses are the control values:

|  | 0 Buffer | 250 Buffer |
| --- | --- | --- |
| MLVs | 91.9% (87.7%) | 84.4% (100.1%) |
| SPLVs | 85.1% (82.7%) | 84.3% (94.2%) |
| MPVs | 85.5% (90.1%) | 75.9% (93.2%) |

As shown by these results, well over 80% of the internal contents of each of the three types of liposomes was retained after the dehydration/rehydration process without the use of any protective sugars. Moreover, adding trehalose to these types of liposomes somewhat decreased, rather than increased, the amount of internal contents retained in the liposomes after the dehydration/rehydration process.

EXAMPLE 8

Dehydration of Liposomes Without The Use of a Protective Sugar: Quantification of Preferred Residual Water Levels This example illustrates that when a liposome preparation is dehydrated without the use of a protective sugar, at least about 2%, and preferably between about 2% and about 5%, of the original water in the preparation should remain in the preparation at the end of the dehydration process so that the liposomes will retain a substantial portion of their internal contents upon rehydration.

The experiments were performed using stable plurilamellar liposomes (SPLVs) and freeze and thaw multilamellar vesicles (FATMLVs), both of which include multiple lipid layers. A detailed description of suitable techniques for producing SPLVs appears in U.S. patent application Ser. No. 476,496, referred to above. See also, Grunner et al., (1985) Biochemistry, 24:2833. A description of techniques for producing FATMLVs can be found in copending and commonly assigned U.S. patent application Ser. No. 752,423, filed July 5, 1985, and entitled "Multilamellar Liposomes Having Improved Trapping Efficiencies," the pertinent portions of which are incorporated herein by reference.

The materials and experimental protocol used were as follows. Egg phosphatidylcholine (99%) was purchased from Avanti Polar Lipids, Inc. (Birmingham, Ala.). [$^{14}$C]inulin and tritiated water were obtained from New England Nuclear (Boston, Mass.). Tritiated water and [$^{14}$C]inulin were counted in a Beckman LS6800 liquid scintillation counter set for 2 channel operation. All data were corrected for isotope counting efficiency and channel spillover.

SPLVs were prepared by adding 400 umoles of egg PC in chloroform to a 100 ml round bottom flask. Bulk solvent was removed by evaporation for approximately 2 minutes using a Rotovap evaporator; the lipid was not taken to dryness. Ten milliliters of anhydrous diethyl ether (J. T. Baker Chemical Co., Phillipsburg, N.J.) was added to the flask to redissolve the lipid. To this solution was added 0.3 ml of equimolar 145 mM NaCl/KCl with 20 mM HEPES (pH 7.4) containing [$^{14}$C]inulin (16.67 uCi/ml, specific activity 2.4 mCi/g) and unlabeled inulin to bring the final inulin concentration to 1.42 umol inulin/0.3 ml buffer. The samples were sonicated for 1 minute for dispersion and then dried with $N_2$ while sonicating until the odor of ether was no longer detectable. The lipid was resuspended in 10 ml of buffer and transferred to a 30 ml Corex tube.

Unentrapped [$^{14}$C]inulin was removed by 4 wash-/centrifugation cycles, the centrifugation being conducted for 30 minutes at $12,100 \times g$ in a Beckman J2-21 centrifuge with a JA-20 rotor. The first wash was performed with 10 ml, and subsequent washes with 20 ml, of buffer.

After decanting the final wash supernatant, the vesicle pellet was resuspended with 5 ml of buffer containing tritiated water (2.5 uCi/ml, specific activity 1 mCi/g). The lipid concentration of this preparation was determined by dividing the amount of lipid used (400 umol) by the measured volume of the preparation. For the SPLV liposomes, the average volume was $6.01 \pm 0.04$ ml, giving an average lipid concentration of $6.65 \times 10^{-5}$ moles lipid/ml.

The radioactivity of the tritiated buffer used to resuspend the vesicles was measured and found to be $5.55 \times 10^6$ dpm/ml (dpm=disintegrations per minute). To be able to calculate residual water values in the dehydrated preparations in terms of moles of water per mole of lipid (see below), this dpm/ml value was converted to a moles $H_2O$/dpm value by dividing the dpm/ml value by the concentration of water in the buffer. For this purpose, the buffer was assumed to be pure water so that the concentration of water was $5.55 \times 10^{-2}$ moles $H_2O$/ml. The moles $H_2O$/dpm value was thus calculated to be $1.00 \times 10^{-8}$ moles $H_2O$/dpm.

After resuspension in the tritiated buffer, the preparation was held for a period of at least 30-60 minutes at room temperature prior to dehydration to allow the tritiated water to equilibrate throughout the preparation.

FATMLVs were prepared by adding 400 umoles of egg PC in chloroform to a 100 ml round bottom flask. Solvent was removed by rotary evaporation for 5 minutes, followed by 2 hours under high vacuum in a dessicator (see dehydration discussion below for a description of the specific equipment used).

The lipid was hydrated with 5 ml of equimolar 145 mM NaCl/KCl and 20 mM Hepes (pH 7.4) containing [$^{14}$C]inulin (1 uCi/ml, specific activity 2.4 mCi/g) and unlabeled inulin to bring the final inulin concentration to 1.08 mM.

The mixture was dispersed by vortexing and aliquots were transferred to 1.8 ml Nunc cryo tubes (Nunc, Denmark). The samples were successively frozen in liquid nitrogen and thawed in warm water five times. The contents were pooled, mixed and transferred to a 30 ml Corex tube.

Unencapsulated [$^{14}$C]inulin was removed by 4 wash-/centrifugation cycles, using 20 ml of buffer for each wash. The centrifugations were performed in the manner described above for SPLVs.

After decanting the final wash supernatant, the vesicle pellet was resuspended with 5 ml of the same tritiated water buffer used to resuspend the SPLVs. The final preparation was held for a period of at least 30-60 minutes prior to dehydration to allow the tritiated water to equilibrate throughout the preparation. As with the SPLV experiments, the lipid concentration of the preparation was determined by dividing the amount of lipid used (400 umol) by the measured volume of the preparation. In this case, the average volume was $7.13 \pm 0.06$ ml, giving an average lipid concentration of $5.60 \times 10^{-5}$ moles lipid/ml.

The radioactivity due to tritiated water of aliquots of the resuspended SPLVs and FATMLVs was measured and an average value of $4.18 \times 10^6 \pm 1.49 \times 10^5$ dpm/ml was obtained for the SPLV suspensions and an average value of $3.60 \times 10^6 \pm 1.41 \times 10^5$ dpm/ml was obtained for the FATMLV suspensions. Using the $1.00 \times 10^{-8}$ moles $H_2O$/dpm value measured for the buffer without vesicles, these radioactivity values were converted to water concentrations for the SPLV and FATMLV suspensions. Specifically, a water concentration of $4.18 \times 10^{-2}$ moles $H_2O$/ml was calculated for the SPLV suspension, and a water concentration of $3.60 \times 10^{-2}$ moles $H_2O$/ml was calculated for the FATMLV suspension. As described below, these values along with the lipid concentrations given above were used to calculate the residual water values in the dehydrated preparation in terms of moles of water per mole of lipid.

In addition to measuring the radioactivity of the resuspended preparations due to tritiated water, the radioactivity due to [$^{14}$C]inulin was also measured.

The preparations were then dehydrated. Specifically, multiple samples were pipetted into 30 ml Corex tubes (approximately 1 ml of suspension per tube), and the weight of the tube plus suspension recorded. The samples were then dried at room temperature under high vacuum with a model D4A Maxima Vacuum Pump (Fisher Scientific, Fairlawn, N.J.) having an ultimate partial pressure rating of $3 \times 10^{-4}$ Torr and a displacement capacity of 127 liters/minute.

The dehydration was carried out for periods of time up to 48 hours, with samples being removed at various points in time and rehydrated with distilled water to their pre-dehydration weight. The vesicles were dispersed by gentle vortexing and the sample was held for approximately 15-30 minutes to allow the tritiated water remaining in the sample after the dehydration process to equilibrate throughout the preparation.

An aliquot was then removed from the sample and its radioactivity per ml due to tritiated water was measured. Percent residual water levels for the dehydrated samples, i.e., the percentage of the original water remaining in the sample after the dehydration process, were then calculated by simply dividing the measured radioactivity levels after rehydration by the average pre-hydration values given above, i.e., by $4.18 \times 10^6$ dpm/ml for SPLVs and $3.60 \times 10^6$ dpm/ml for FATMLVs.

The percent residual water values were converted to moles of water per mole of lipid in the dehydrated preparation by multiplying the percent values by the water concentrations given above, i.e., by $4.18 \times 10^{-2}$ moles H$_2$O/ml for SPLVs and by $3.60 \times 10^{-2}$ moles H$_2$O/ml for FATMLVs, and dividing by the lipid concentrations, i.e., by $6.65 \times 10^{-5}$ moles lipid/ml for SPLVs and $5.60 \times 10^{-5}$ moles lipid/ml for FATMLVs. For example, the calculated values obtained for the integer percentages between 1 and 6 percent were:

| % residual water | water/lipid ratio | |
| --- | --- | --- |
| | SPLV | FATMLV |
| 6.0 | 37.7/1 | 38.6/1 |
| 5.0 | 31.4/1 | 32.1/1 |
| 4.0 | 25.2/1 | 25.7/1 |
| 3.0 | 18.9/1 | 19.3/1 |
| 2.0 | 12.6/1 | 12.9/1 |
| 1.0 | 6.3/1 | 6.4/1 |

After the radioactivity of the rehydrated preparation due to tritiated water had been measured, inulin retention was determined by first subjecting the rehydrated sample to 3 wash/centrifugation cycles using 10 milliliters of buffer per wash. The centrifugation was performed for 25 minutes at $12,100 \times g$ using the equipment described above. The vesicles in the final wash pellet were resuspended to their original weight with buffer and assayed for [$^{14}$C]inulin. Percent inulin retained values were calculated by dividing the post-rehydration radioactivity values by the pre-dehydration values.

Figure 9:
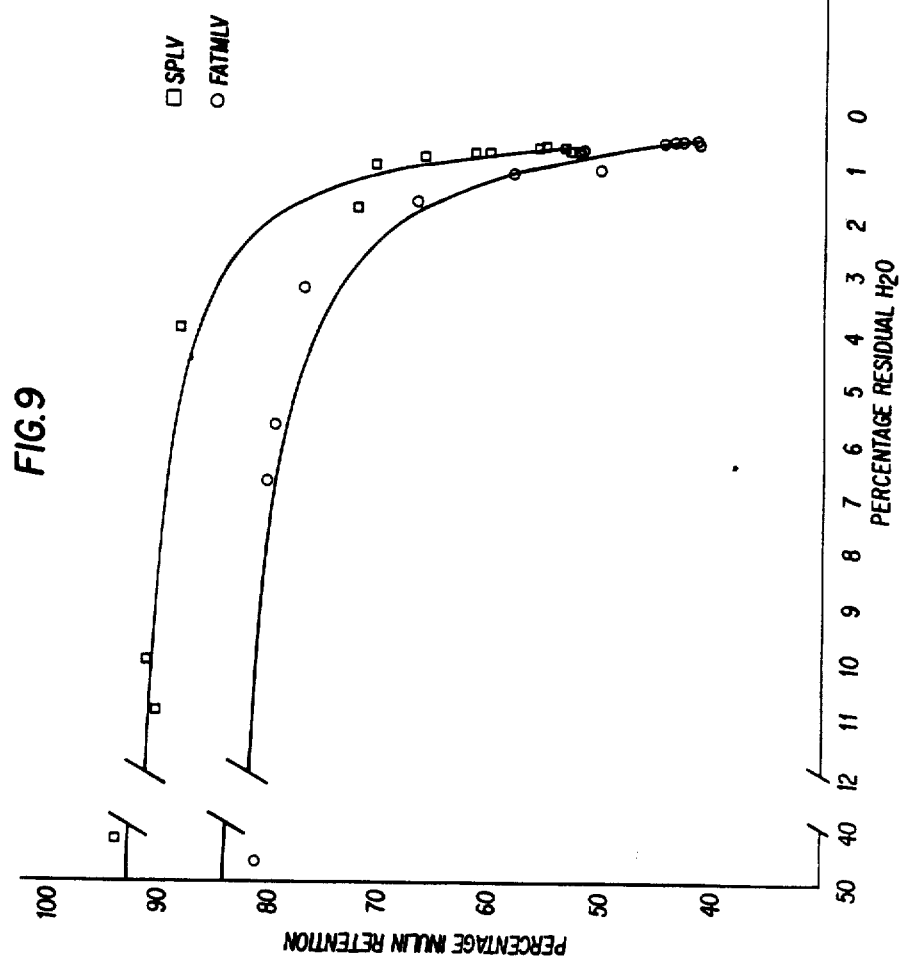
FIG. 9 shows the retention of inulin in freeze and thaw multilamellar vesicles (FATMLVs) and stable plurilamellar vesicles (SPLVs) as a function of the percentage of the original water remaining in the preparation at the end of the dehydration process. The liposomes were dehydrated in the absence of protective sugars under reduced pressure.

The results of these experiments are shown graphically in FIG. 9. As shown therein, the percent inulin retained values remain relatively constant down to a residual water level of about 5%, i.e., a moles of water/moles of lipid value for the dehydrated preparation on the order of 35. Thereafter, increasingly greater amounts of inulin loss are seen with reduced residual water levels, with losses on the order of 30–40% and more being seen once the residual water level drops below about 2.0%, i.e., a moles of water/moles of lipid value for the dehydrated preparation on the order of 12.

Since for long-term storage, it is in general desirable to have a minimal amount of water in the preparation, these results demonstrate that to achieve this goal and still have reasonably low levels of vesicle rupture, the residual water level in the dehydrated preparation should preferably be kept between about 2% and about 5%, or in terms of moles of water per mole of lipid, between about 12 moles H$_2$O/mole lipid and about 35 moles H$_2$O/mole lipid.

EXAMPLE 9

Dehydration of Liposomes Without The Use of a Protective Sugar: Effects of Vesicle Type, Lipid Type and Lipid Concentration This example illustrates the effects of vesicle type, lipid type, and lipid concentration on the dehydration of liposomes without a protective sugar.

SPLVs and FATMLVs were prepared as described in Example 8 with the following changes: (1) both egg PC and soy PC (Avanti Polar Lipids, Birmingham, Ala.) were used; (2) the starting amount of lipid was either 400 umoles, as in Example 8, or 15 umoles; (3) 1.0 uCi/ml tritiated water was added to the buffer, rather than 2.5 uCi/ml tritiated water; and (4) in the case of SPLVs, inulin and radioactive inulin were added both in accordance with the procedures of Example 8 and by adding [$^{14}$C]inulin (3.34 uCi/ml, specific activity 2.4 mCi/g) and unlabelled inulin to bring the final inulin concentration to 1.08 umol inulin/0.3 ml buffer. With regard to this last change, it was found that the measured values of retained inulin were indistinguishable for the two radioactive inulin preparations.

MPVs were prepared following the procedures of U.S. patent application Ser. No. 521,176, referred to above in Example 7. Specifically, either 15 or 400 umoles of egg PC or soy PC in chloroform were added to a 100 ml round bottom flask. The solvent was removed by rotary evaporation for 5–10 minutes, followed by 30 minutes under high vacuum using the equipment described in Example 8. Five milliliters of 100% ethanol was added to the flask to resolubilize the lipids. To this solution was added 0.30 ml of equimolar 145 mM NaCl/KCl with 20 mM HEPES (pH 7.4) containing [$^{14}$C]inulin (16.67 uCi/ml, specific activity 2.4 mCi/g) and unlabeled inulin to bring the final inulin concentration to 1.42 umol inulin/0.3 ml buffer. The contents of the flask were mixed by vortexing, and the mixture was dried to a thin film by rotary evaporation for 5–10 minutes, followed by 30 minutes under high vacuum, again using the equipment of Example 8. The lipid was resuspended in 5 ml of buffer and transferred to a 30 ml Corex tube.

Unincorporated [$^{14}$C]inulin was removed by 4 wash/centrifugation cycles, using 20 milliliters of buffer for each wash. Centrifugation was performed for 30 minutes as described in Example 8. After decanting the final wash supernatant, the vesicle pellet was resuspended with 5 ml of buffer containing tritiated water (1.0 uCi/ml, specific activity 1 mCi/g). The preparation was then held for a period of at least 30–60 minutes prior to dehydration to allow for equilibration of the tritiated water throughout the preparation.

MLVs were prepared by adding either 15 or 400 umoles of egg PC or soy PC in chloroform to a 100 ml round bottom flask. Solvent was removed by rotary evaporation for 5 minutes, followed by 2 hours under high vacuum, using the equipment of Example 8. The lipid was hydrated with 5 ml of equimolar 145 ml NaCl/KCl with 20 mM HEPES (pH 7.4) containing [$^{14}$C]inulin (1.0 uCi/ml, specific activity 2.4 mCi/g) and unlabeled inulin to bring the final inulin concentration to 1.08 mM. The lipid was dispersed by vortexing and the suspension was allowed to swell for 2 hours. Unsequestered [$^{14}$C]inulin was removed and tritiated water was added following the procedures described above for MPVs.

One milliliter samples of the sixteen preparations (a high concentration EPC, a low concentration EPC, a high concentration SPC, and a low concentration SPC for SPLVs, FATMLVs, MPVs and MLVs) were placed in 30 ml Corex tubes and dried in a dessicator for 2 days at room temperature under high vacuum using the vacuum pump described in Example 8. Another set of samples were lyophilized. Specifically, 1 ml samples were frozen using the shell freezing technique in 30 ml Corex tubes and then dried overnight in a model FDX-1-84-D Flexi-dry lyophilization unit (FTS Systems, Inc., Stone Ridge, N.Y.). Control samples (1 ml in 30 ml Corex tubes) were covered and left at room temperature for 2 days.

Percent inulin retention and percent residual water were determined following the procedures and using the equipment described in Example 8. The results are shown in Table 6.

A comparison of the inulin retention values for the various preparations reveals that: (1) formulations having a high phospholipid concentration prior to dehydration suffer less damage (i.e., less leakage of the internal contents of the liposomes) than formulations having a low phospholipid concentration; (2) egg PC vesicles generally suffer less damage than soy PC vesicles; and (3) MPVs generally suffer less damage than SPLVs and FATMLVs. In addition, the data shows that freezing of the preparation prior to dehydration (the "lyophilization" experiments) results in significantly more damage to the vesicles than does dehydration without prior freezing (the "vacuum dessication" experiments), irrespective of vesicle type, lipid type, or lipid concentration.

Although specific embodiments of the invention have been described and illustrated, it is to be understood that modifications can be made without departing from the invention's spirit and scope. For example, liposome preparation techniques other than those used in the examples can be used to prepare the liposomes which are to be dehydrated and then rehydrated. Similarly, charged materials other than adriamycin can be loaded into liposomes using a transmembrane potential.

TABLE 1

Ability of Dehydrated Vesicles to Retain Adriamycin

| | Adriamycin Content (nmoles/μmole lipid) |
|---|---|
| Before dehydration | 197 |
| Immediately after dehydration and rehydration | 185 |
| One hour after dehydration and rehydration | 158 |
| Two hours after dehydration and rehydration | 145 |

ETVs were prepared using a solute solution containing adriamycin and 250 mM trehalose. The samples were dehydrated for 24 hours without prior freezing. The adriamycin content of the initial sample and the rehydrated vesicles was determined as described in Example 1.

TABLE 2

| Sample | Drying Time (Hrs.) | $^{22}Na^+$ retained % | Residual water % |
|---|---|---|---|
| Trehalose on both sides of membrane (250 mM) | 24 | 94 | 5.6 |
| | 48 | 84 | 5.4 |
| | 72 | 84 | 5.2 |
| Trehalose on outside of membrane (250 mM) | 24 | 68 | 5.4 |
| | 48 | 49 | 5.0 |
| | 72 | 17 | 4.2 |

TABLE 3

Influence of Vesicle Size on Ability to Retain $^{22}Na^+$

| Polycarbonate filter pore size (nm) | Vesicle mean diameter (nm) | % $^{22}Na^+$ retained following dehydration and rehydration |
|---|---|---|
| 800 | 500 | 80% |
| 400 | 220, 500 | 84% |
| 200 | 180, 375 | 87% |
| 100 | 170 | 92% |

TABLE 3-continued

Influence of Vesicle Size on Ability to Retain $^{22}Na^+$

| Polycarbonate filter pore size (nm) | Vesicle mean diameter (nm) | % $^{22}Na^+$ retained following dehydration and rehydration |
|---|---|---|
| 50 | 112 | 88% |

Vesicles were prepared with varying mean diameters by extruding multilamellar vesicles through polycarbonate filters of appropriate diameters (see "Materials and Methods"). The samples all contained 250 mM trehalose and were dehydrated for 24 hours without prior freezing.

TABLE 4

Comparison of the Ability of Different Sugars To Stabilize Vesicles in the Anhydrous State

| Sugar tested (500 mM) | % $^{22}Na^+$ retained following dehydration and rehydration |
|---|---|
| Trehalose | 88% |
| Glucose | 73% |
| Sucrose | 86% |
| Maltose | 76% |
| Lactose | 66% |

Large unilamellar vesicles were prepared in the presence of 500 mM of each sugar, dehydrated for 24 hours without prior freezing, and the amount of trapped $^{22}Na^+$ retained upon rehydration determined as described in "Materials and Methods".

TABLE 5

Ability of Streptomycin to Protect Vesicles During Dehydration-Rehydration

| | % $^3H$—Inulin Retained | |
|---|---|---|
| | Control | Freeze-Dried |
| PBS | 97 | 36 |
| PBS plus 52 mM streptomycin | 92 | 31 |
| PBS plus 568 mM streptomycin | 94 | 86 |

Monophasic vesicles were prepared and washed in the presence and absence of streptomycin, dehydrated under vacuum with prior freezing, and rehydrated as described in Example 5. The control vesicles were stored at room temperature for the same periods of time as used for the freeze-drying process (24 hours).

TABLE 6

Inulin Retention as a Function of Vesicle Type, Lipid Type and Lipid Concentration

| Lipid Concentration | Vacuum Dessication | Lyophilization | Control |
|---|---|---|---|
| MPV | | | |
| EPC (low) | 47.0 ± 0.5 | 27.1 ± 3.1 | 86.6 ± 6.1 |
| EPC (high) | 63.9 ± 6.0 | 58.3 ± 1.7 | 101.3 ± 1.8 |
| SPC (low) | 41.0 ± 3.5 | 29.2 ± 5.3 | 71.7 ± 10.1 |
| SPC (high) | 54.6 ± 5.4 | 42.4 ± 1.8 | 96.9 ± 2.2 |
| MLV | | | |
| EPC (low) | 44.6 ± 14.7 | 40.7 ± 24.6 | N.D. |
| EPC (high) | 62.0 ± 3.8 | 55.4 ± 5.8 | 99.8 ± 2.1 |
| SPC (low) | 28.4 ± 10.1 | 18.3 ± 3.9 | N.D. |
| SPC (high) | 60.4 ± 2.2 | 53.8 ± 3.3 | 98.4 ± 7.8 |
| SPLV | | | |
| EPC (low) | 31.3 ± 0.6 | 17.0 ± 3.8 | 69.3 ± 7.5 |
| EPC (high) | 56.4 ± 1.9 | 54.4 ± 3.5 | 98.5 ± 2.8 |
| SPC (low) | 37.2 ± 2.9 | 24.6 ± 0.2 | 87.6 ± 1.0 |
| SPC (high) | 48.4 ± 6.2 | 44.6 ± 2.3 | 97.8 ± 1.7 |
| FATMLV | | | |
| EPC (low) | 35.6 ± 4.2 | 18.4 ± 2.6 | 102.1 ± 4.9 |
| EPC (high) | 54.9 ± 0.1 | 34.8 ± 7.7 | 95.3 ± 0.4 |
| SPC (low) | 24.6 ± 12.2 | 24.4 ± 1.6 | 89.8 ± 11.4 |

TABLE 6-continued

Inulin Retention as a Function of
Vesicle Type, Lipid Type and Lipid Concentration

| Lipid Concentration | Vacuum Dessication | Lyophilization | Control |
|---|---|---|---|
| SPC (high) | 43.7 ± 6.0 | 27.9 ± 0.7 | 96.1 ± 1.4 |

Values reported = % of original inulin retained in the preparation after dehydration and rehydration ± S.D.
N.D. = Not determined.
Low lipid concentration = 3 umol lipid hydrated with 1 ml prior to dehydration.
High lipid concentration = 80 umol lipid hydrated with 1 ml prior to dehydration.
Drying Time - Vacuum Dessication -- 2 days - Lyophilization -- 1 day (residual water levels after dehydration equaled approximately 2% or less for both procedures)
Number of experiments per data point = 2; data corrected for blank, 2 channel spillover; EPC = Egg PC; SPC = Soy PC.

What is claimed is:

1. A dehydrated liposome preparation comprising liposomes having a bilayer membrane and one or more protective sugars, wherein the protective sugars are present at both the inside and outside surfaces of the liposome membrane so that the liposomes have retained a substantial portion of their internal contents during dehydration and retain a substantial portion of their contents upon subsequent rehydration.

2. The preparation of claim 1 wherein the one or more protective sugars are disaccharide sugars.

3. The preparation of claim 1 wherein the one or more sugars are selected from the group consisting of trehalose, maltose, sucrose, glucose, lactose, and dextran.

4. The preparation of claim 3 wherein the sugar is trehalose.

5. The preparation of claim 3 wherein the sugar is sucrose.

6. The preparation of claim 1 wherein the one or more protective sugars are aminoglycosides.

7. The preparation of claim 6 wherein the sugar is streptomycin.

8. The preparation of claim 6 wherein the sugar is dihydrostreptomycin.

9. The preparation of claim 1 wherein the internal contents comprise a drug.

* * * * *

UNITED STATES PATENT AND TRADEMARK OFFICE
CERTIFICATE OF CORRECTION

PATENT NO.   : B1 4,880,635
DATED        : July 2, 1996
INVENTOR(S)  : Andrew S. Janoff et al It is certified that error appears in the above-indentified patent and that said Letters Patent is hereby corrected as shown below:

Column 2, Line 18, Claim 18, delete "hydrataed" and insert therefor --dehydrated--.

Column 2, Line 29, Claim 19, delete "53" and insert therefor --18--.

Signed and Sealed this

Seventeenth Day of December, 1996

Attest:

BRUCE LEHMAN

*Attesting Officer*   *Commissioner of Patents and Trademarks*

US004880635B1

REEXAMINATION CERTIFICATE (2937th)

United States Patent [19]
Janoff et al.

[11] B1 4,880,635
[45] Certificate Issued Jul. 2, 1996

[54] DEHYDRATED LIPOSOMES

[75] Inventors: Andrew S. Janoff, Yardley, Pa.; Pieter R. Cullis; Marcel B. Bally, both of Vancouver, Canada; Michael W. Fountain, Griggstown; Richard S. Ginsberg, Monroe, both of N.J.; Michael J. Hope; Thomas D. Madden, both of Vancouver, Canada; Hugh P. Schieren, Yardley, Pa.; Regina L. Jablonski, Trenton, N.J.

[73] Assignee: Liposome Company, Inc., Princeton, N.J.

Reexamination Request:
No. 90/003,125, Jul. 13, 1993

Reexamination Certificate for:
Patent No.: 4,880,635
Issued: Nov. 14, 1989
Appl. No.: 759,419
Filed: Jul. 26, 1985

Related U.S. Application Data

[63] Continuation-in-part of Ser. No. 638,809, Aug. 8, 1984, abandoned, and Ser. No. 749,161, Jun. 26, 1985, abandoned.

[51] Int. Cl.⁶ .......................... A61K 9/127; A61K 9/133
[52] U.S. Cl. ........................................................... 424/450
[58] Field of Search .................... 424/450; 428/402.2; 439/829

[56] References Cited

U.S. PATENT DOCUMENTS

| | | | |
|---|---|---|---|
| 3,962,429 | 6/1976 | Furuno et al. | 424/181 |
| 4,053,585 | 10/1977 | Allison et al. | 424/92 |
| 4,193,983 | 3/1980 | Ullman et al. | 424/12 |
| 4,217,344 | 8/1980 | Vanlerberghe et al. | 424/60 |
| 4,229,360 | 10/1980 | Schneider et al. | 260/403 |
| 4,235,871 | 11/1980 | Papahadjopoulos et al. | 424/19 |
| 4,241,046 | 12/1980 | Papahadjopoulos et al. | 424/19 |
| 4,247,411 | 1/1981 | Vanlerberghe et al. | 424/450 |
| 4,370,349 | 1/1983 | Evans et al. | 424/365 |
| 4,389,330 | 6/1983 | Tice et al. | 427/213.36 |
| 4,397,846 | 8/1983 | Welner et al. | 424/199 |
| 4,411,894 | 10/1983 | Schrank et al. | 424/199 |
| 4,438,052 | 3/1984 | Weder et al. | 264/4.6 |
| 4,469,577 | 7/1984 | Moro et al. | 424/180 |
| 4,485,045 | 11/1984 | Regen | 260/403 |
| 4,485,054 | 11/1984 | Mezei et al. | 264/4.6 |
| 4,515,736 | 5/1985 | Deamer | 264/4.3 |

FOREIGN PATENT DOCUMENTS

| | | |
|---|---|---|
| 0094692 | 11/1983 | European Pat. Off. |
| 3335701 | 4/1984 | Germany |
| 2002319 | 2/1979 | United Kingdom |
| 2041871 | 9/1980 | United Kingdom |
| 2134869 | 8/1984 | United Kingdom |
| 1575344 | 9/1990 | United Kingdom |
| WO86/00238 | 1/1986 | WIPO |
| WO91/00084 | 1/1991 | WIPO |

OTHER PUBLICATIONS

Bangham in Methods in Membrane Biology Plenum Press N.Y. (1974) pp. 1–68.
Deamer, Liposome Prep: Methods and Mechanisms Liposmes, Chap. I, 1983 pp. 27–51.
Deamer, 1983, in: *Liposomes*, M. Ostro, (ed.) Marcel Dekker, Inc., New York, "Method for Encapsulating Materials into Liposomes".
Bally, et al., 2985, Biochim. Biophys. Acta., 812:66, "Uptake of safranine and other lipophilic cations into model membrane systems in response to a membrane potential".
Gruner, 1985, Biochemistry, 24:2833, "Novel Multilayered Lipid Vesicles: Comparison of Physical Characteristics of Multilamellar Liposomes and Stable Plurilamellar Vesicles".
Garcia, et al., Biochemistry, 1983, 22(10):2524, "Mechanism of Lactose Translocation in Proteoliposomes Reconstituted with lac Carrier Protein Purified from *Eshericia coli*. 1. Effect of pH and Imposed Membrane Potential on Efflux, Exchange, and Counterflow".
Shakhov, et al., 1984, Biokhimika, 48(8):1347, "Reconstitution of Highly Purified Proton–Translocating Pyrothosphatase".
Kirby, et al., 1984, Bio/Technology, 2(11):979 "Dehydration–Rehydration Vesicles: A Simple Method for High Yield Drug Entrapment in Liposomes".
Crommelen, et al., 1983, Int. J. Pharm., 16(1):79, "Preparation and characterization of doxorubicin–containing liposomes: I. Influence of liposome charge and pH of hydration medium on loading capacity and particle size".
van Hoesel, et al., 1984, Cancer Res., 44:3698, "Reduced Cardiotoxicity and Nephrotoxicity with Preservation of Antitumor Activity of Doxorubicin Entrapped in Stable Liposomes in the LOU/M Wsi Rat".
Crommelin, et al., 1983, Int. J. Pharm., 17(2–3):135, Preparation and characterization of doxorubicin–containing liposomes. II. Loading capacity, long–term stability and doxorubicin–bilayer interation mechanism.
U. Pick, "Liposomes With A Large Trapping Capacity Prepared By Freezing And Thawing Of Sonicated Phospholipid Mixtures", Archives of Biochemistry and Biophysics, vol. 212, No. 1, pp. 186–194 (1981).

(List continued on next page.)

*Primary Examiner*—Gollamudi S. Kishore

[57] ABSTRACT

Dehydrated liposomes are prepared by drying liposome preparations under reduced pressure in the presence of one or more protective sugars, e.g., the disaccharides trehalose and sucrose. Preferably, the protective sugars are present at both the inside and outside surfaces of the liposome membranes. Freezing of the liposome preparation prior to dehydration is optional. Alternatively, the protective sugar can be omitted if: (1) the liposomes are of the type which have multiple lipid layers; (2) the dehydration is done without prior freezing; and (3) the dehydration is performed to an end point which results in sufficient water being left in the preparation (e.g., at least 12 moles water/mole lipid) so that the integrity of a substantial portion of the multiple lipid layers is retained upon rehydration. Concentration gradients capable of generating transmembrane potentials can be created across the liposome membranes either before or after dehydration, and the transmembrane potentials resulting from these gradients can be used to load charged materials, e.g., drugs, into the liposomes.

OTHER PUBLICATIONS

Kirby and Gregoriadis, "A Simple Procedure For Preparing Liposomes Capable of High Encapsulation Efficiency Under Mild Conditions" in Liposome Technology vol. 1, Preparation Of Liposomes, Chapter 2, pp. 20–20 (1984).

J. Crowe, et al., "Preservation of Structural and Functional Activity In Lyophilized Sarcoplasmic Reticulum", Archives of Biochemistry and Biophysics, vol. 220, No. 2, pp. 477–484 (1983).

L. M. Crowe et al., "Effects of Carbohydrates on Membrane Stability at Low Water Activities", Biochemica et Biophysica Acta, 769: 141–150 (1984).

J. H. Crowe, et al., "Preservation of Membranes in Anhydrobiotic Organisms: The Role of Trehalose", Science, vol. 223, pp. 701–703 (1984).

J. H. Crowe, et al., "Infrared Spectroscopic Studies on Interactions of Water and Carbohydrates with a Biological Membrane", Archives of Biochemistry and Biophysics, vol. 232, No. 1, 400–407 (1984).

J. H. Crowe, et al., "Interactions of Phospholipid Monolayers with Carbohydrates", Biochimica et Biophysica Acta, 769: 151–159 (1984).

C. Wormersley, et al., "Inhibition of and Dehydration-Induced Fusion Between Liposome by a Carbohydrates", Biophysical Journal vol. 45: 191a (1984).

Racker, E., "Reconstitution of Cytochrome Oxidase Vesicles and Conferral of Sensitivity to Energy Transfer Inhibitors", J. Membrane Biol. 10:221–235 (1972).

Gordon et al., "Lyophilization–A Means of Increasing Shelf–Life of Phospholipid Bi–Layer Vesicles", Drug Development and Industrial Pharmacy, 8(4), 465–473 (1982).

F. Puisieux et al., "Les Liposomes, Formes Pharmaceutiques du Futur", Sciences & Techniques, No., 318:133–151 (1982).

F. Szoka, et al., "Comparative Properties and Methods of Preparation of Lipid Vesicles (Liposomes)", Ann. Rev. Biophys. Bioeng. 9:467–508 (1980).

Shulkin, et al., "Lyophilized Liposomes: a new method for long–term vesicular storage", J. Microencapsulation, vol. 1, No. 1, 73–80 (1984).

Morris et al., "The Response of Multilamellar Liposomes to Freezing and Thawing", Cryobiology 18:390–398 (1981).

Crommelin et al., "Stability of Liposomes on Storage: Freeze Dried, Frozen or as an Aqueous Dispersion", Pharmaceutical Research, 1(4):159–163 (1984).

V. Roman et al., "Preservation of Liposomes by Lyophilization", S.S.A. Trav. Scient. 4:241–243 (1983).

Siminovitch et al., "Liposome Bilayer Model Systems of Freezing Living Cells", FEBS Letters 16(3):207–212 (1917).

Strauss et al., "Stabilization of Liposomes Bilayers to Freezing and Thawing: Effects of Cryoprotective Agents and Membrane Proteins", Cryobiology 17:508–515 (1980).

G. Morris, "Liposomes as a Model System for Investigating Freezing Injury" in Effects of Low Temperature on Biological Membranes (Morris & Clarke Ed.), Academic Press, New York and London, 241–262 (1981).

G. Morris, "The Response of Liposomes to Various Rates of Cooling to −196° C.: Effect of Phospholipid: Cholesterol Ratio", Cryobiology 19, 215–218 (1982).

J. McGrath, "Cryomicroscopy of Liposome Systems as Simple Models to Study Cellular Freezing Response", Cryobiology 21, 81–92 (1984).

G. F. Doebbler and A. P. Rinfret, "The Influence of Protective Compounds and Cooling and Warming Conditions on Hemolysis of Erythrocytes by Freezing and Thawing", Biochimica et Biophysica Acta, 58, 449–458 (1962).

S. Kim, et al., "Preparation of Cell–Size Unilamellar Liposomes with High Captured Volume and Defined Size Distribution", Biochimica et Biophysics Acta, 646 1–9 (1981).

H. H. Hub, et al., "Preparation of Large Unilamellar Vesicles", FEBS Letters, vol. 140, No. 2, pp. 254–256 (1982).

C. Tremblay, et al., "Efficacy of Liposome–Intercalated Amphotericin B in the Treatment of Systemic Candidiasis in Mice", Antimicrobial Agents and Chemotherapy, vol. 26, No. 2, pp. 170–173 (1984).

H. Talsma, et al., "Liposomes as Drug Delivery Systems, Part I: Prepration", Pharmaceutical Technology, Oct. 1992.

"Liposomes–A Practical Approach", R. R. New (Ed.) Oxford University Press, pp. 23–24 (1990).

The Merck Index, 10th Edition, pp. 401, 859, 860 (1983).

F. Szoka, et al., "Liposomes: Preparation and Characterization", in From Physical Structure to Therapeutic Applications, Knight (Ed.) Elsevier, pp. 51–82 (1981).

S. Kaye, "Liposomes–Problems and Promise as Selective Drug Carriers", Cancer Treatment Reviews, 8:27–50 (1981).

Forssen, et al., "Use of Anionic Liposomes For The Reduction of Chronic Doxorubicin–induced Cardiotoxicity", Proc. Nat. Acad. Sci. USA, vol. 78, No. 3, pp. 1873–1877 (1981).

D. Lichtenberg, et al., "Liposomes: Preparation, Characterization, and Preservation" in Methods of Biochemical Analysis, vol. 33, Glick (Ed.), Wiley Interscience, New York, pp. 337–462 (1988).

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 6–8 are cancelled.

Claims 1–5 and 9 are determined to be patentable as amended.

New claims 10–28 and 29 are added and determined to be patentable.

1. A dehydrated liposome preparation comprising *unilamellar* liposomes having a bilayer membrane and one or more protective sugars, wherein *protective concentrations of* the protective sugars are present at both the inside and outside surfaces of the liposome membrane so that the liposomes have retained [a substantial portion] *at least about 66%* of their internal contents during dehydration and [retain a substantial portion of their contents upon] subsequent rehydration *and wherein the liposomes upon rehydration are about 112 nm*.

2. The preparation *according to any one* of [claim] *claims 1, 17 or 18* wherein the one or more protective sugars are disaccharide sugars.

3. The preparation *according to any one* of [claim] *claims 1, 17 or 18* wherein the one or more sugars are selected from the group consisting of trehalose, maltose, sucrose, glucose, lactose, and dextran.

4. The preparation *according to any one* of [claim] *claims 3, 17 or 18* wherein the sugar is trehalose.

5. The preparation *according to any one* of [claim] *claims 3, 17 or 18* wherein the sugar is sucrose.

9. The preparation *according to any one* of [claim] *claims 1, 17 or 18* wherein the internal contents comprise a drug.

*10. The dehydrated liposome preparation of claim 1 in which the liposomes have retained at least 73% of their internal contents.*

*11. The dehydrated liposomes preparation of claim 1 in which the liposomes have retained at least 86%.*

*12. The dehydrated liposome preparation of claim 1 in which the liposomes have retained at least 94% of their internal contents.*

*13. A dehydrated liposome preparation comprising liposomes having a bilayer membrane and one or more protective sugars selected from the group consisting of the aminoglycosides streptomycin and dihydrostreptomycin, wherein the protective sugars are present at both the inside and outside surfaces of the liposome membrane so that the liposomes have retained a substantial portion of their internal contents during dehydration and retain a substantial portion of their internal contents upon subsequent rehydration.*

*14. The dehydrated liposome composition according to claim 13 wherein the sugar is an aminoglycoside.*

*15. The dehydrated liposome composition according to claim 13 wherein the sugar is streptomycin.*

*16. The dehydrated liposome composition according to claim 13 wherein the sugar is dihydrostreptomycin.*

*17. A dehydrated liposome preparation comprising unilamellar liposomes having a bilayer membrane and one or more protective sugars, wherein protective concentrations of the protective sugars are present at both the inside and outside surfaces of the liposome membrane so that the liposomes have retained at least 66% of their internal contents during dehydration and subsequent rehydration and wherein the unilamellar liposomes are greater than 50 nm as measured upon rehydration and as determined by freeze fracture in the presence of 25% glycerol.*

*18. A hydydrataed liposome preparation comprising unilamellar liposomes having a bilayer membrane and one or more protective sugars, wherein protective concentrations of the protective sugars are present at both the inside and outside surfaces of the liposome membrane so that the liposomes have retained at least about 66% of their internal contents during dehydration and subsequent rehydration and wherein the unilamellar liposomes upon rehydration are greater than 50 nm as determined using quasi-elastic light scattering.*

*19. The dehydrated liposome preparation according to any one of claims 17 or 53, wherein the unilamellar liposomes are greater than about 60 nm.*

*20. The dehydrated liposome preparation of claim 17 in which the liposomes have retained at least 73% of their internal contents.*

*21. The dehydrated liposome preparation of claim 17 in which the liposomes have retained at least 86% of their internal contents.*

*22. The dehydrated liposome preparation of claim 17 in which the liposomes have retained at least 94% of their internal contents.*

*23. The dehydrated liposome preparation of claim 18 in which the liposomes have retained at least 73% of their internal contents.*

*24. The dehydrated liposome preparation of claim 18 in which the liposomes have retained at least 86% of their internal contents.*

*25. The dehydrated liposome preparation of claim 18 in which the liposomes have retained at least 94% of their internal contents.*

*26. The dehydrated liposome preparation of claim 19 in which the liposomes have retained at least 73% of their internal contents.*

*27. The dehydrated liposome preparation of claim 19 in which the liposomes have retained at least 86% of their internal contents.*

*28. The dehydrated liposome preparation of claim 19 in which the liposomes have retained at least 94% of their internal contents.*

*29. The preparation to any of claims 1, 17 or 18 wherein the liposomes upon rehydration have a uniform size distribution.*

* * * * *